United States Patent [19]

Raddatz et al.

[11] Patent Number: 5,147,857

[45] Date of Patent: Sep. 15, 1992

[54] GLYCOLIC ACID DERIVATIVES

[75] Inventors: Peter Raddatz, Darmstadt; Claus J. Schmitges, Gross-Umstadt; Klaus-Otto Minck, Ober-Ramstadt, all of Fed. Rep. of Germany

[73] Assignee: Merck Patent Gesellschaft Mit Beschraenkter Haftung, Darmstadt, Fed. Rep. of Germany

[21] Appl. No.: 670,677

[22] Filed: Mar. 18, 1991

[30] Foreign Application Priority Data

Jun. 16, 1990 [DE] Fed. Rep. of Germany ....... 4008403

[51] Int. Cl.$^5$ .................... A61K 37/00; C07D 413/00; C07D 265/30
[52] U.S. Cl. ...................... 514/19; 544/139; 544/160; 546/210; 546/224; 546/226; 530/316; 530/330; 530/331; 514/18
[58] Field of Search ............... 546/194, 210, 226, 224; 544/139, 160; 530/316, 331, 330; 514/18, 19

[56] References Cited

U.S. PATENT DOCUMENTS

| | | | |
|---|---|---|---|
| 4,804,743 | 2/1989 | Kaltenbronn et al. | 530/330 |
| 4,870,183 | 9/1989 | Iizuka et al. | 546/210 |
| 4,880,781 | 11/1989 | Hester, Jr. et al. | 514/18 |
| 4,963,530 | 10/1990 | Hemmi et al. | 514/19 |
| 4,986,845 | 1/1991 | Oya et al. | 71/92 |
| 5,022,916 | 6/1991 | Willms et al. | 544/60 |

FOREIGN PATENT DOCUMENTS

| | | |
|---|---|---|
| 0300189 | 1/1989 | European Pat. Off. . |
| 376819 | 7/1990 | European Pat. Off. . |
| 417698 | 3/1991 | European Pat. Off. . |

OTHER PUBLICATIONS

Chemical Abstracts 114:74652 (1991).

Primary Examiner—Mukund J. Shah
Assistant Examiner—Matthew V. Grumbling
Attorney, Agent, or Firm—Millen, White & Zelano

[57] ABSTRACT

New glycolic acid derivatives of the formula I $$X-O-CR^1R^2-CO-Y-NR^3-CHR^4-CR^5-CH_2-CR^6R^7-Z \quad I$$

in which $R^1$ to $R^7$, X, Y and Z have the meanings indicated herein, and salts thereof, inhibit the activity of human plasma renin.

20 Claims, No Drawings

GLYCOLIC ACID DERIVATIVES

SUMMARY OF THE INVENTION

Glycolic acid derivatives of the formula I $$X-O-CR^1R^2-CO-Y-NR^3-CHR^4-CR^5-CH_2-CR^6R^7-Z \quad \text{I}$$

in which

X is $R^8$, $R^8-O-C_mH_{2m}-CO-$, $R^8-C_mH_{2m}-O-CO-$, $R^8-C_mH_{2m}-CO-$, $R^8-SO_2-$, $R^9R^{10}N-C_mH_{2m}-CO-$, $R^{11}-NH-C(=NH)-NH-C_mH_{2m}-CO-$, $R^9OOC-C_mH_{2m}-CO-$, $R^9O_3S-C_mH_{2m}-CO-$, $R^9-O-(CH_2CH_2O)_n-C_mH_{2m}-CO-$ or $An^\ominus N^\oplus A_3-C_mH_{2m}-CO-$, Y is 0 or 1 amino acid residue selected from the group comprising Abu, Ada, Ala, βAla, Arg, Asn, Asp, Bia, Cal, Cys, S—A—Cys, Dab, Gln, Glu, Gly, His, N(im)—A—His, Hph, Ile, Leu, tert.-Leu, Lys, Mal, Met, αNal, βNal, Nbg, Nle, Nve, Orn, Phe, Pia, Pro, Pya, Ser, Thr, Tia, Tic, Trp, Tyr and Val, Z is $-CN_2-NR^{12}-COR^{14}$, $-CH_2-NR^{12}-SO_2R^{14}$, $-CH_2-NR^{12}-COR^{14}$, $-CH_2-NR^{12}-CO-NH-R^{14}$ or $-CH_2-NR^{12}-C-S-NH-R^{14}$, $R^1$, $R^3$, $R^6$, $R^7$, $R^9$, $R^{10}$, $R^{12}$ and $R^{13}$ are each H or A, $R^2$, $R^4$, $R^8$ and $R^{14}$ are each H, A, Ar, Ar-alkyl, Het, Het-alkyl, cycloalkyl having 3–7 C atoms, cycloalkylalkyl having 4–11 C atoms, bicycloalkyl or tricycloalkyl each having 7–14 C atoms, or bicycloalkylalkyl or tricycloalkylalkyl each having 8–18 C atoms, wherein said cycloalkyl, cycloalkylalkyl, bicycloalkyl, tricycloalkyl, bicycloalkylalkyl and tricycloalkylalkyl groups are unsubstituted or singly or multiply substituted by A, AO and/or Hal, $R^5$ is (H, OH), (H, NH$_2$) or =O, $R^{11}$ is H, A or CN, $R^9R^{10}N$ and $NR^{12}R^{13}$ are also each a pyrrolidino, piperidino, morpholin or piperazino group which is unsubstituted or is substituted by A, OH, NH$_2$, NHA, NA$_2$, NHAc, NH—CO—C$_x$H$_{2x}$—O—R$^{15}$, NH—CO—O—C$_2$H$_{2x}$—O—R$^{15}$, hydroxyalkyl, COOH, COOA, CONH$_2$, aminoalkyl, HAN-alkyl, A$_2$N-alkyl, A$_3$N$^\ominus$alkyl An$^\oplus$, NH—CO—NH$_2$, NH—CO—NHA, guanidinyl or guanidinylalkyl, $R^{15}$ is A or Ar-alkyl, m, n and x are each 0, 1, 2, 3, 4, 5, 6, 7, 8, 9 or 10, Ar is phenyl which is unsubstituted or is substituted one or more times by A, OA, Hal, CF$_3$, OH, NO$_2$, hydroxyalkyl, NH$_2$, NHA, NA$_2$, NHAc, NH—SO$_2$—A, SA, SO—A, SO$_2$—A, SO$_2$NH$_2$, SO$_2$NHA, COOH, COOA, CONH$_2$, CN, aminoalkyl, HAN-alkyl, A$_2$N-alkyl, A$_3$N$^\oplus$alkyl An$^{63}$ and-/or guanidinylalkyl, or is unsubstituted naphthyl, Het is a saturated or unsaturated 5- or 6-membered heterocyclic radical which has 1–4 N, O and/or S atoms and can be fused with a benzene ring and/or be substituted one or more times by A, OA, Hal, CF$_3$, OH, NO$_2$, carbonyl oxygen, NH$_2$, NHA, NA$_2$, NHAc, NH—COOA, NHCOOAr, NHCOOCH$_2$Ar, NH—SO$_2$—A, SA, SO—A, SO$_2$—A, SO$_2$NH$_2$, SO$_2$NHA, COOH, COOA, CONH$_2$, CN, Ar, Ar-alkyl, Ar-alkenyl, hydroxyalkyl, aminoalkyl, HAN-alkyl, A$_2$N-alkyl, and/or A$_3$N$^\oplus$alkyl An$^\ominus$, and/or whose N and/or S hetero atoms can also be oxidized, Hal is F, Cl, Br or I, Ac is A—CO—, Ar—Co—, Ar—alkyl—CO— or A—NH—CO—, An$^\ominus$is an anion, which can also be absent if, in its place, a carboxyl group contained in the compound of the formula I is in the form of a carboxylate anion, —alkyl— is an alkylene group having 1–8 C atoms, and A is alkyl having 1–8 C atoms, in which, furthermore, it is also possible for one or more —NH—CO— groups to be replaced by one or more —NA— CO— groups, as well as the salts thereof.

In the foregoing, selection of variables defined together is made independently.

Similar compounds are disclosed in EP-A 249,096.

An object of the invention is to provide new compounds with valuable properties, in particular those which can be used for the preparation of medicaments.

Upon further study of the specification and appended claims, further objects and advantages of this invention will become apparent to those skilled in the art.

It has been found that the compounds of the formula I and the salts thereof have very valuable properties. In particular, they inhibit the activity of human plasma renin. This action can be detected, for example, by the method of F. Fyhrquist et al., Clin.Chem. 22, 250–256 (1976). The noteworthy point is that these compounds are very specific inhibitors of renin; as a rule, the concentrations of these compounds necessary for the inhibition of other aspartyl proteinases (for example pepsin and cathepsin D) are about 100 to 1000 times as high as for renin inhibition. The actions of the compounds on the blood pressure and/or on the heart rate, as well as the inhibition of renin activity in blood plasma can furthermore be determined in conscious monkeys, for example female monkeys (Macaca fascicularis); it is possible in this for the blood pressure and heart rate to be measured by a modification of the method of M. J. Wood et al., J. Hypertension 4, 251-254 (1985). In order to stimulate renin activity in this, the animals are preferably pretreated with a saluretic. Blood samples for the determination of the plasma renin activity can be obtained by puncture of the femoral vein.

The compounds can be used as pharmaceutically active substances in human and veterinary medicine, in particular for the prophylaxis and for the treatment of diseases of the heart, circulation and vessels, especially of hypertension, cardiac insufficiency and hyperaldosteronism. In addition, the compounds can be used for diagnostic purposes in order to determine, in patients with hypertension or hyperaldosteronism, the possible contribution of the renin activity to maintaining the pathological state. The procedure for such diagnostic tests can be similar tot hat indicated in EP-A 77,028.

The abbreviations quoted hereinbefore and hereinafter for amino acid residues represent the radicals —NR'—R''—CO—, as a rule —NH—CHR—CO— (in which R, R' and R'' have the specific meaning known for each amino acid), of the following amino acids:

| Abu | 2-aminobutyric acid |
| Ada | 3-(1-adamantyl)-alanine |
| Ala | alanine |

|   |   |
|---|---|
| βAla | β-alanine |
| Arg | arginine |
| Asn | asparagine |
| Asp | aspartic acid |
| Bia | 3-(2-benzimidazolyl)-alanine |
| Cal | 3-cyclohexylalanine |
| Cys | cysteine |
| S-A-Cys | S-alkyl-cysteine |
| S-Me-Cys | S-methyl-cysteine |
| Dab | 2,4-diaminobutyric acid |
| Gln | glutamine |
| Glu | glutamic acid |
| Gly | glycine |
| His | histidine |
| N(im)-A-His | histidine substituted in the 1 or 3 position of the imidazole ring by A |
| Hph | homophenylalanine (2-amino-4-phenylbutyric acid) |
| Ile | isoleucine |
| Leu | leucine |
| tert.-Leu | tert.-leucine |
| Lys | lysine |
| Mal | 3-(p-methoxyphenyl)-alanine |
| Met | methionine |
| αNal | 3-(α-naphthyl)-alanine |
| βNal | 3-(β-naphthyl)-alanine |
| Nbg | 2-norbornyl-glycine |
| Nle | norleucine |
| N-Me-His | N-methyl-histidine |
| N-Me-Phe | N-methyl-phenylalanine |
| Nva | norvaline |
| Orn | ornithine |
| Phe | phenylalanine |
| Pia | 3-(piperidyl)-alanine [e.g., 2-Pia = 3-(2-piperidyl)-alanine] |
| Pro | proline |
| Pya | 3-(pyridyl)-alanine [e.g., 3-Pya = 3-(3-pyridyl)-alanine] |
| Ser | serine |
| Thr | threonine |
| Tia | 3-(thienyl)-alanine [e.g., 2-Tia = 3-(2-thienyl)-alanine] |
| Tic | 1,2,3,4-tetrahydroisoquinoline-1-carboxylic acid |
| Trp | tryptophan |
| Tyr | tyrosine |
| Val | valine. |
| Further meanings hereinafter are: | |
| BOC | tert.-butoxycarbonyl |
| BOM | benzyloxymethyl |
| imi-BOM | benzyloxymethyl in the 1 position of the imidazole ring |
| CBZ | benzyloxycarbonyl |
| DCCI | dicyclohexylcarbodiimide |
| DMF | dimethylformamide |
| DNP | 2,4-dinitrophenyl |
| imi-DNP | 2,4-dinitrophenyl in the 1 position of the imidazole ring |
| ETOC | ethoxycarbonyl |
| FMOC | 9-fluorenylmethoxycarbonyl |
| HOBt | 1-hydroxybenzotriazole |
| IPOC | isopropoxycarbonyl |
| Pla | the radical of phenyllactic acid —O—CH(CH$_2$C$_6$H$_5$)—CO— (S form) |
| POA | phenoxyacetyl |
| THF | tetrahydrofuran |
| TFA | trifluoroacetate. |

If the abovementioned amino acids can occur in several enantiomeric forms, then all these forms, as well as mixtures thereof (for example the DL forms), are included hereinbefore and hereinafter, for example as constituents of the compounds of the formula I. The L-forms are preferred. Where individual compounds are mentioned hereinafter, then the abbreviations of these amino acids each relate to the L-form unless expressly indicated otherwise.

The invention furthermore relates to a process for the preparation of a glycolic acid derivative of the formula I, and of the salts thereof, characterized in that it is liberated from one of its functional derivatives by treatment with a solvolyzing or hydrogenolyzing agent, or in that a carboxylic acid of the formula II $$X-G^1-OH \qquad \qquad II$$

in which $G^1$ is
(a) absent,
(b) —O—CR$^1$R$^2$—CO—,
(c) —O—CR$^1$R$^2$—CO—Y—,
or one of the reactive derivatives thereof, is reacted with a compound of the formula III $$H-G^2-NH^3-CHR^4-CR^5-CH_2-CR^6R^7-Z \qquad III$$

in which $G^2$ is
(a) —O—CR$^1$R$^2$—CO—Y—,
(b) —Y—,
(c) absent,
and in that a functionally modified amino and/or hydroxyl group in a compound of the formula I is liberated where appropriate by treatment with solvolyzing or hydrogenolyzing agents, and/or a free amino group is acylated by treatment with an acylating agent and/or for the preparation of a compound of the formula I, $R^5$=(H, OH) or (H, NH$_2$), an amino keto acid derivative of the formula I, $R^5$=O, is reduced or reductively aminated, and/or a compound of the formula I is converted by treatment with an acid into one of the salts thereof.

Hereinbefore and hereinafter the radicals and parameters $R^1$ to $R^{15}$, X, Y, Z, m, n, x, Ar, Het, Hal, Ac, An$^\ominus$, A, $G^1$ and $G^2$ have the meanings indicated for the formulae I, II or III unless expressly indicated otherwise.

A in the abovementioned formulae has 1-8, preferably 1, 2, 3 or 4 C atoms. A is preferably methyl, furthermore ethyl, propyl, isopropyl, butyl, isobutyl, sec.-butyl or tert.-butyl, as well as pentyl, 1-, 2- or 3-methylbutyl, 1,1-, 1,2- or 2,2-dimethylpropyl, 1-ethylpropyl, hexyl, 1-, 2-, 3- or 4-methylpentyl, 1,1-, 1,2-, 1,3-, 2,2-, 2,3- or 3,3-dimethylbutyl, 1- or 2-ethylbutyl, 1-ethyl-1-methylpropyl, 1-ethyl-2-methylpropyl, 1,1,2- or 1,2,2-trimethylpropyl, heptyl or octyl.

Typically, all "alkyl", and "alkenyl" portions mentioned above have up to 8 C atoms, including, for example, the alkylene and alkenylene portions of Ar-alkenyl, Ar-alkyl, guanidinyl-alkyl, HAN-alkyl, A$_2$N-alkyl, and hydroxyalkyl.

Cycloalkyl is preferably cyclopropyl, cyclobutyl, cyclopentyl, cyclohexyl or cycloheptyl, but is also, for example, 1-, 2- or 3-methylcyclopentyl, or 1-, 2-, 3- or 4-methylcyclohexyl.

Correspondingly, cycloalkylalkyl is preferably cyclopropylmethyl, 2-cyclopropylethyl, cyclobutylmethyl, 2-cyclobutylethyl, cyclopentylmethyl, 2-cyclopentylethyl, cyclohexylmethyl, 2-cyclohexylethyl, but is also, for example, 1-, 2- or 3-methylcyclopentylmethyl, or 1-, 2-, 3- or 4-methylcyclohexylmethyl.

Bicycloalkyl is preferably 1- or 2-decalyl, 2-bicyclo[2.2.1]heptyl or 6,6-dimethyl-2-bicyclo[3,1,1]heptyl.

Tricycloalkyl is preferably 1-adamantyl.

Hal is preferably F, Cl or Br, but is also I.

Ac is preferably A—CO—, such as acetyl, propionyl or butyryl, Ar—CO— such as benzoyl, o-, m- or p-methoxybenzoyl or 3,4-dimethoxybenzoyl, or A—N-H—CO— such as N-methyl- or N-ethylcarbamoyl.

Ar is preferably phenyl and is furthermore preferably o-, m- or op-tolyl, o-, m- or p-ethylphenyl, o-, m- or p-methoxyphenyl, o-, m- or p-fluorophenyl, o-, m- or p-chlorophenyl, o-, m- or p-bromophenyl, o-, m- or p-iodophenyl, o-, m- or p-trifluoromethylphenyl, o-, m- or p-hydroxyphenyl, o-, m- or p-sulfamoyphenyl, 2,3-, 2,4-, 2,5-, 2,6-, 3,4- or 3,5-dimethoxyphenyl, 3,4,5-trimethoxyphenyl, o-, m- or p-aminophenyl, o-, m- or p-aminomethylphenyl, o-, m- or p-dimethylaminomethylphenyl, o-, m- or p-guandidnomethylphenyl, or 1- or 2-naphthyl.

Correspondingly, Ar-alkyl is preferably benzyl, 1- or 2-phenylethyl, o-, m- or p-methylbenzyl, 1- or 2-o-, -m- or -p-tolylethyl, o-, m- or p-ethylbenzyl, 1- or 2-o-, -m- or -p-ethylphenylethyl, o-, m- or p-methoxybenzyl, 1- or 2-o-, -m- or -p-methoxyphenylethyl, o-, m- or p-fluorobenzyl, 1- or 2-o-, -m- or -p-fluorophenylethyl, o-, m- or p-chlorobenzyl, 1- or 2-o-, -m- or -p-chlorophenylethyl, o-, m- or p-bromobenzyl, 1- or 2-o-, -m- or -p-bromophenylethyl, o-, m- or p-iodobenzyl, 1-or 2-o-, -m- or -p-iodophenylethyl, o-, m- or p-trifluoromethylbenzyl, o-, m- or p-hydroxybenzyl, 2,3-, 2,4-, 2,5-, 2,6- 3,4- or 3,5-dimethoxybenzyl, 3,4,5-trimethoxybenzyl, o-, m- or p-aminobenzyl, o-, m- or p-aminomethylbenzyl, o-, m- or p-dimethylaminomethylbenzyl, o-, m- or p-guanidnomethylbenzyl, or 1- or 2-naphthylmethyl.

Het is preferably 2- or 3-furyl, 2- or 3-thienyl, 1-, 2- or 3-pyrrolyl, 1-, 2-, 4- or 5-imidazolyl, 1-, 3-, 4- or 5-pyrazolyl, 2-, 4- or 5-oxazolyl, 3-, 4- or 5-isoxazolyl, 2-, 4- or 5-thiazolyl, 3-, 4- or 5-isothiazolyl, 2-, 3- or 4-pyridyl, 2-, 4-, 4- or 6-pyrimidinyl, furthermore preferably 1,2,3-triazol-1-, -4- or -5-yl, 1,2,4-triazol-1-, -3- or -5-yl, 1- or 5-tetrazolyl, 1,2,3-oxadiazol-4- or -5-yl, 1,2,4-oxadiazol-3- or -5-yl, 1,3,4-thiadiazol-2- or -5-yl, 1,2,4-thiadiadol-3- or 5-yl, 2,1,5-thiadiazol-3- or -4-yl, 2-, 3-, 4-, 5- or 6-2H-thiopyranyl, 2-, 3- or 4-4H-thiopyranyl, 3- or 4-pyridazinyl, pyrazinyl 2-, 3-, 4-, 5-, 6- or 7-benzofuryl, 2-, 3-, 4-, 5-, 6- or 7-benzothienyl, 1-, 2-, 3-, 4-, 5-, 6- or 7-indolyl, 1-, 2-, 3-, 4-, 5-, 6- or 7-isoindolyl, 1-, 2-, 4- or 5-benzimidazolyl, 1-, 3-, 4-, 5-, 6- or 7-benzopyrazolyl, 2-, 4-, 5-, 6- or 7-benzoxazolyl, 3-, 4-, 5-, 6- or 7-benzisoxazolyl, 2-, 4-, 5-, 6- or 7-benzothiazolyl, 2-, 4-, 5-, 6- or 7-benzothiazolyl, 4-, 5-, 6- or 7-benz-2,1,3-oxadiazolyl, 2-, 3-, 4-, 5-, 6-, 7- or 8-quinolyl, 1-, 3-, 4-, 5-, 6-, 7- or 8-isoquinolyl, 1-, 2-, 3-, 4- or 9-carbazolyl, 1-, 2-, 3-, 4-, 5-, 6-, 7-, 8- or 9-acrindinyl, 3-, 4-, 5-, 6-, 7- or 8-cinnolyl, 2-, 4-, 5-, 6-, 7- or 8-quinazolyl. The heterocyclic radicals can also be partially or completely hydrogenated. Thus, Het can also be, for example, 2,3-dihydro-2-, -3-, -4-, or -5-furyl, 2,5-dihydro-2-, -3-, -4- or -5-furyl, tetrahydro-2- or 3-furyl, tetrahydro-2- or -3-thientyl, 2,3-dihydro-1-, -2-, -3-, -4- or -5-pyrrolyl, 2,5-dihydro-1-, -2-, -3-, -4- or -5-pyrrolyl, 1-, 2-, or 3-pyrrolidinyl, tetrahydro-1-, -2- or -4-imidazolyl, 2,3-dihydro-1-, -2-, -3-, -4- or -5-pyrazolyl, tetrahydro-1-, -3- or -4-pyrazolyl, 1,4-dihyrdo-1-, -2-, -3- or -4-pyridyl, 1,2,3,4-tetrahydro-1-, -2-, -3-, -4-, -5- or -6-pyridyl, 1,2,3,6-tetrahydro-1-, -2-, -3, -4-, -5- or -6-pyridyl, 1-, 2-, 3- or 4-piperidinyl, 2-, 3- or 4-morpholinyl, tetrahydro-2-, -3- or -4-pyranyl, 1,3-dioxanyl, 1,3-dioxan-2-, -4- or -5-yl, hexahydro-1-, -3-, or -4-pyridazinyl, hexahydro-1-, -2, -4- or -5-pyrimidinyl, 1-, 2- or 3-piperazinyl, 1,2,3,4-tetrahydro-1-, -2-, -3-, -4-, -5-, -6-, -7- or -8-quinolyl, 1,2,3,4-tetrahydro-1-, -2-, -3-, -4-, -5-, -6-, -7- or -8-isoquinolyl.

The heterocyclic radicals can also be substituted as indicated. Het can also preferably be, for example, 2-amino-4-thiazolyl, 4-carboxy-2-thiazolyl, 4-carbamoyl-2-thiazolyl, 4-(2-aminoethyl)-2-thiazolyl, 4-amino-2-methyl-5-pyrimidinyl, 2-amino-5,6-dimethyl-3-pyrazinyl, 4-carbamoylpiperidino, furthermore, for example, 3-, 4- or 5-methyl-2-furyl, 2-, 4- or 5-methyl-3-furyl, 2,4-dimethyl-3-furyl, 5-nitro-2-furyl, 5-styryl-2-furyl, 3-, 4- or 5-methyl-2-thienyl, 2-, 4- or 5-methyl-3-thienyl, 3-methyl-5-tert.-butyl-2-thienyl, 5-chloro-2-thienyl, 5-phenyl-2- or -3-thienyl, 1-, 3-, 4- or 5-methyl-2-pyrrolyl, 1-methyl-4- or 5-nitro-2-pyrrolyl, 3,5-dimethyl-4-ethyl-2-pyrrolyl, 4-methyl-5-pyrazolyl, 5-methyl-3-isoxazolyl, 3,4-dimethyl-5-isoxazolyl, 4- or 5-methyl-2-thiazolyl, 2- or 5-methyl-4-thiazolyl, 2- or 4-methyl-5-thiazolyl, 2,4-dimethyl-5-thiazolyl, 3-, 4-, 5-, or 6-methyl-2-pyridyl, 2-, 4-, 5- or 6-methyl-3-pyridyl, 2- or 3-methyl-4-pyridyl, 3-, 4-, 5- or 6-chloro-2-pyridyl, 2-, 4-, 5- or 6-chloro-3-pyridyl, 2- or 3-chloro-4-pyridyl, 2,6-dichloropyridyl, 2-hydroxy-3-, -4-, -5- or -6-pyridyl (=1H-2-pyridon-3-, -4-, -5- or -6-yl), 5-phenyl-1H-2-pyridon-3-yl, 5-p-methoxyphenyl-1H-2-pyridon-3-yl, 2-methyl-3-hydroxy-4-hydroxymethyl-5-pyridyl, 2-hydroxy-4-amino-6-methyl-3-pyridyl, 3-N'-methylureido-1H-4-pyridon-5-yl, 4-methyl-2-pyrimidinyl, 4,6-dimethyl-2-pyrimidinyl, 2-, 5- or 6-methyl-4-pyrimidinyl, 2,6-dimethyl-4-pyrimidinyl, 2,6-dihydroxy-4-pyrimidinyl, 5-chloro-2-methyl-4-pyrimidinyl, 3-methyl-2-benzofuryl, 2-ethyl-3-benzofuryl, 7-methyl-2-benzothienyl, 1-, 2-, 4-, 5-, 6- or 7-methyl-3-indolyl, 1-methyl-5- or -6-benzimidazolyl, 1-ethyl-5- or -6-benzimidazolyl, 3-, 4-, 5-, 6-, 7- or 8-hydroxy-2-quniolyl, 2-oxo-pyrrolidino, 2-oxopiperidino, 2,5-dioxopyrrolidino or 3-benzyl-2,5-dioxopyrrolidino.

X is, in general preferably $R^8$, $R^8-C_mH_{2m}-O-CO-$, $R^9-R^{10}N-C_mH_{2m}-CO-$, in particular 4-BOC-amino-piperidinocarbonyl or 4-aminopiperidinocarbonyl.

The group Y preferably consists of one of the stated amino acid residues; however, it can also be absent. Y is preferably His, Leu or S-Me-Cys, furthermore preferably β-Ala, Asn, N-Me-His, Met, Nle, Nva, Pya (especially 3-Pya), Tia or Val.

Z is, in general, preferably $-CN$, $-CH_2-NR^{12}-SO_2R^{14}$ or $-CH_2-NR^{12}-CO-NHR^{14}$, furthermore preferably $-CH_2-NR^{12}-CS-HNR^{14}$ or $-CH_2-NR^{12}-COR^{14}$.

$R^1$, $R^3$, $R^6$, $R^7$, $R^9$, $R^{10}$, $R^{12}$ and $R^{13}$ are each preferably H and furthermore preferably methyl; $R^6$ is also preferably isopropyl or isobutyl, $R^9R^{10}N$ is also preferably pyrrolidino, piperidino, morpholino, aminopiperidino such as 4-aminopiperidino, alkylaminopiperidino such as 4-methylaminopiperidino, or dialkylaminopiperidino such as 4-dimethylaminopiperidino, or BOC-aminopiperidino such as 4-BOC-aminopiperidino.

$R^2$ is preferably Ar-alkyl, especially benzyl or p-methoxybenzyl; furthermore preferably A, especially n-butyl or isobutyl; cycloalkyl-alkyl, especially cyclohexylmethyl; Het-alkyl, especially 2-thienylmethyl. The group $-O-CR^1R^2-CO-$ is preferably the radical Pla.

$R^4$ is preferably cycloalkylalkyl, especially cyclohexylmethyl, furthermore preferably alkyl, especially n-butyl or isobutyl; Ar-alkyl, especially benzyl or p-methoxybenzyl; Het-alkyl, e.g. 2-thienylmethyl; cycloalkyl, especially cyclohexyl.

$R^5$ is preferably (H, OH).

$R^8$ is preferably A, especially ethyl, ethyl, isopropyl or tert.-butyl; or Ar, especially phenyl, 1- or 2-naphthyl.

$R^{11}$ is preferably H, methyl or CN.

$R^{14}$ is preferably A, especially methyl, ethyl, propyl, isopropyl, butyl, isobutyl, sec.-butyl, tert.-butyl, pentyl or isopentyl; H; cycloalkylalkyl, especially cyclohexylmethyl; Ar-alkyl, especially benzyl; Ar, especially phenyl or aminophenyl such as p-aminophenyl.

$R^{15}$ is preferably A having 1–4 C atoms, especially isopropyl or tert.-butyl; or Ar-alkyl, especially benzyl.

The parameter m is preferably 1, 2, 3, 4 or 5; n is preferably 1; x is preferably 1 or 2.

$C_mH_{2m}$ and $C_xH_{2x}$ are preferably straight-chain and thus are preferably —$(CH_2)_m$— or —$(CH_2)_x$—.

Accordingly, the group X is preferably A, e.g. isopropyl or isobutyl; Ar-alkyl, e.g. benzyl; $R^8$—$(CH_2)_m$—O—CO—, e.g. BOC or CBZ; $R^9R^{10}N$—$(CH_2)_m$—CO—, especially $H_2N$—$C_mH_{2m}$—CO— such as aminocarbonyl, aminoacetyl (H-Gly)-, 3-aminopropionyl (H-βAla-), 4-aminobutyryl, 5-aminopentanoyl, 6-aminohexanoyl, 7-aminoheptanoyl, 8-aminooctanoyl, 9-aminononanoyl, 10-aminodecanoyl, 11-aminoundecanoyl, but also, for example, 2-aminopropioinyl (Ala), 2-amino-2-methylpropionyl; ANH-$C_mH_{2m}$—CO— such as methylaminocarbonyl, methylaminoacetyl (sarcosyl), 3-methylaminopropionyl, 4-methylaminobutyryl, 5-methylaminopentanoyl, 6-methylaminohexanoyl, 6-ethylaminohexanoyl, 7-methylaminoheptanoyl, 8-methylaminooctanoyl, 9-methylaminononanoyl, 10-methylaminodecanoyl, 11-methylaminoundecanoyl; $A_2N$—$C_mH_{2m}$—CO— such as dimethylaminocarbonyl, dimethylaminoacetyl, 3-dimethylaminopropionyl, 4-dimethylaminobutyryl, 5-dimethylaminopentanoyl, 6-dimethylaminohexanoyl, 6-diethylaminohexanoyl, 7-dimethylaminoheptanoyl, 8-dimethylaminooctanoyl, 9-dimethylaminononanoyl, 10-dimethylaminodecanoyl, 11-dimethylaminoundecanoyl; pyrrolidino—$C_mH_{2m}$CO— such as pyrrolidinocarbonyl, pyrrolidinoacetyl, 3-pyrrolidinopropionyl, 4-pyrrolidino-butyryl, 5-pyrrolidino-pentanoyl, 6-pyrrolidino-hexanoyl, 7-pyrrolidino-heptanoyl, 8-pyrrolidino-octanoyl, 9-pyrrolidino-nonanoyl, 10-pyrrolidino-decanoyl; piperidino—$C_mH_{2m}$—CO— such as piperidinocarbonyl, piperidinoacetyl, 3-piperidinopropionyl, 4-piperidinobutyryl, 5-piperidino-pentanoyl 6-piperidino-hexanoyl, 7-piperidino-heptanoyl, 8-piperidino-octanoyl, 9-piperidino-nonanoyl, 10-piperidinodecanoyl; morpholino—$C_mH_{2m}$—CO— such as morpholinocarbonyl, morpholinoacetyl, 3-morpholino-propionyl, 4-morpholinobutyryl, 5-morpholino-pentanoyl, 6-morpholino-hexanoyl, 7-morpholino-heptanoyl, 8-morpholino-octanoyl, 9-morpholino-nonanoyl, 10-morpholino-decanoyl; 4-amino-piperidino—$C_mH_{2m}$—CO— such as 4-amino-piperidino-carbonyl, 4-amino-piperidino-acetyl, 3-(4-amino-piperidino)-propionyl, 4(4-amino-piperidino)-butyryl, 5-(4-aminopiperidino)-pentanoyl, 6-(4-amino-piperidino)-hexanoyl, 7(4-amino-piperidino)-heptanoyl, 8-(4-amino-piperidino)octanoyl, 9-(4-amino-piperidino)-nonanoyl, 10-(4-aminopiperidino)-decanoyl; 4-dialkylamino-piperidino—$C_mH_{2m}$—CO— such as 4-dimethylamino-piperidinocarbonyl, 4-dimethylamino-piperidino-acetyl; 4-guanidino-piperidino—$C_mH_{2m}$—CO— such as 4-guanidino-piperidino-carbonyl, 4-guanidinopiperidino-acetyl; 4-carboxy-piperidino—$C_mH_{2m}$—CO— such as 4-carboxy-piperidino-carbonyl, 4-carboxy-piperidinoacetyl; 4-alkoxycarbonyl-piperidino—$C_mH_{2m}$—CO— such as 4-methoxycarbonyl-piperidino-carbonyl, 4-ethoxycarbonylpiperidino-carbonyl, 4-methoxycarbonylpiperidino-acetyl, 4-ethoxycarbonyl-piperidino-acetyl; 4-AcNH-piperidino—$C_mH_{2m}$—CO— such as 4-acetamido-piperidino-carbonyl, 4-acetamidopiperidino-acetyl; $H_2N$—C(=NH)—NH—$C_mH_{2m}$—CO— such as guanidinoacetyl, 3-guanidino-propionyl, 4-guanidinobutyryl, 5-guanidino-pentanoyl, 6-guanidino-hexanoyl, 7-guanidino-heptanoyl, 8-guanidino-octanoyl; NC—NH—C(=NH)—NH—$C_mH_{2m}$—CO— such as N'-cyanoguanidino-acetyl, 3-(N'-cyanoguanidino)-propionyl, 4-(N'-cyanoguanidino)butyryl, 5-(N'-cyanoguanidino)-pentanoyl, 6-(N'-cyanoguanidino)-hexanoyl, 7-(N'-cyanoguanidino)-heptanoyl, 8-(N'-cyanoguanidino)-octanoyl; HOOC—$C_mH_{2m}$—CO— such as malonyl, succinyl, glutaryl, adiphyl, 6-carboxyhexanoyl, 7-carboxyheptanoyl, 8-carboxyoctanoyl, 9-carboxynonanoyl, 10-carboxydecanoyl, 11-carboxyundecanoyl; AOOC—$C_mH_{2m}$—CO— such as methoxycarbonylacetyl, 3-methoxycarbonylpropionyl, 4-methoxycarbonyl-butyryl, 5-methoxycarbonylpentanoyl, 6-methoxycarbonyl-hexanoyl, 7-methoxycarbonylheptanoyl, 8-methoxycarbonyl-octanoyl, 9-methoxycarbonylnonanoyl, 10-methoxycarbonyl-decanoyl, ethoxycarbonylacetyl, 3-ethoxycarbonyl-propionyl, 4-ethoxycarbonylbutyryl, 5-ethoxycarbonyl-pentanoyl, 6-ethoxycarbonylhexanoyl, 7-ethoxycarbonyl-heptanoyl, 8-ethoxycarbonyloctanoyl, 9-ethoxycarbonyl-nonanoyl, 10-ethoxycarbonyldecanoyl; H—$SO_3$—$C_mH_{2m}$— such as suflo-acetyl, 3-sulfopropionyl, 4-sulfo-butyryl, 5-pentanoyl, 6-sulfohexanoyl, 7-sulfo-heptanoyl, 8-sulfooctanoyl, 9-sulfononanoyl, 10-sulfo-decanoyl; A—$SO_3$—$C_mH_{2m}$—CO— such as methoxysulfonyl-acetyl, 3-methoxysulfonyl-propionyl, 4-methoxysulfonyl-butyryl, 5-methoxysulfonyl-pentanoyl, 6-methoxysulfonylhexanoyl, 7-methoxyfulfonyl-heptanoyl, 8-methoxysulfonyl-octanoyl, 9-methoxyfulfonyl-nonanoyl, 10-methoxysulfonyl-decanoyl, ethoxysulfonyl-acetyl, 3-ethoxysulfonyl-propionyl, 4-ethoxysulfonyl-butyryl, 5-ethoxysulfonyl-pentanoyl, 6-ethoxysulfonyl-hexanoyl, 7-ethoxysulfonyl-heptanoyl, 8-ethoxysulfonyloctanoyl, 9-ethoxysulfonyl-nonanoyl, 10-ethoxysulfonyl-decanoyl; $R^8$—$C_mH_{2m}$—O—CO— especially A—O—CO— such as ETOC, IPOC, BOC as well as Ar—$C_mH_{2m}$—O—CO— such as CBZ; $R^8$—$C_mH_{2m}$—CO— such as 3,3-dimethylbutyryl.

. Accordingly, the group Z if preferably —CN; —$CH_2NH$—$SO_2R^{14}$, especially —$CH_2$—NH—$SO_2$—A such as methane-, ethane-, propane-, 2-methylpropane- and butane-sulfonamidomethyl, furthermore, for example, phenylmethane- and cyclohexylmethane-sulfonamidomethyl; —$CH_2$—NH—CO—NH—$R^{14}$, especially —$CH_2NH$—CO—NH—A such as N'-methylureidomethyl, N'-ethylureidomethyl, N'-propylureidomethyl, N'isopropylureidomethyl, N'-butylureidomethyl, N'-isopentylureidomethyl, furthermore —$CH_2$—NH—CO—NH—Ar such as N'-phenylureidomethyl and N'-p-aminophenylureidomethy; —$CH_2$—NH—CS—NH—$R^{14}$, especially —$CH_2$—NH—CH—NH—A such as N'-methylthioureidomethyl; —$CH_2$—NH—$COR^{14}$, especially —$CH_2NH$—CO—A such as acetaminomethyl, propionamidomethyl, butyramidomethyl and isovaleramidomethyl.

The compounds of the formula I may have one or more chiral centers and therefore exist in various, optically active or optically inactive, forms. The formula I embraces all these forms. If $R^4$ is different from H, and/or $R^5$ is (H, OH) or (H, $NH_2$), the 4S-hydroxy, 4S-amino, 5S-amino, 4S-hydroxy-5S-amino and 4S,4S- diamino enantiomers are preferred (where the C atom which carries the radical $R^5$ is assigned to the 4 position and that which carries the radicals X—O—$CR^1$—$R^2$—CO—Y—$NR^3$ and $R^4$ is assigned to the 5 positions).

The abovementioned cyclic groups, especially the cycloalkyl and phenyl groups, are preferably unsubstituted or carry preferably 1 to 3, especially 1 or 2, substituents.

Accordingly, the invention particularly relates to those compounds of the formula I in which at least one of the said radicals has one of the preferred meanings indicated hereinbefore. Some preferred groups of compounds can be represented by the following part-formulae Ia to Ik:

Ia $R^8$—O—$CR^1R^2$—CO—Y—$NR^3$—$CHR^4$—$CR^5$—$CH_2$—$CR^6R^7$—Z;

Ib $R^8$—O—$C_mH_{2m}$—CO—O—$CR^1R^2$—CO—Y—$NR^3$—$CHR^4$—$CR^5$—$CH_2$—$CR^6R^7$—Z;

Ic $R^8$—$C_mH_{2m}$—O—CO—O—$CR^1R^2$—CO—Y—$NR^3$—$CHR^4CR^5$—$CH_2$—$CR^6R^7$—Z;

Id $R^8$—$C_mH_{2m}$—CO—O—$CR^1R^2$—CO—Y—$NR^3$—$CHR^4$—$CR^5$—$CH_2$—$CR^6R^7$—Z;

Ie $R^9R^{10}N$—$C_mH_{2m}$—CO—O—$CR^1R^2$—CO—Y—$NR^3$—$CHR^4$—$CR^5$—$CH_2$—$CR^6R^7$—Z;

If $R^{11}$—NH—C(=NH)—NH—$C_mH_{2m}$—CO—O—$CR^1R^2$—CO—Y—$NR^3$—$CHR^4$—$CR^5$—$CH_2$—$CR^7R^7$—Z;

Ig $R^9OOC$—$C_mH_{2m}$—CO—O—$CR^1R^2$—CO—Y—$NR^3$—$CHR^4$—$CR^5$—$CH_2$—$CR^6R^7$—Z;

Ih $R^9O_3S$—$C_mH_{2m}$—CO—O—$CR^1R^2$—CO—Y—$NR^3$—$CHR^4$—$CR^5$—$CH_2$—$CR^6R^7$—Z;

Ii $R^9$—O—$(CH_2CH_2O)_n$—$C_mH_{2m}$—CO—O—$CR^1R^2$—CO—Y—$NR^3$—$CHR^4$—$CR^5$—$CH_2$—$CR^6R^7$—Z;

Ij $R^9R^{10}N$—CO—O—$CR^1R^2$—CO—Y—$NR^3$—$CHR^4$—$CR^5$—$CH_2$—$CR^6R^7$—Z;

Ik 4-Aminopiperidinocarbonyl—O—$CR^1R^2$—CO—Y—$NR^3$—$CHR^4$—$CR^5$—$CH_2$—$CR^6R^7$—Z.

Particularly preferred are compounds of the part-formulae:

(a) Iaa to Ika, which correspond to the formulae Ia to Ik but in which additionally —O—$CR^1R^2$—CO— is Pla;

(b) Iab to Ikb and Iaab to Ikab, which correspond to the formulae Ia to Ik and Iaa to Ika but in which additionally Y is His, Leu or S—Me—Cys;

(c) Iac to Ikc, Iaac to Ikac, Iabc to Ikbc and Iaabc to Ikabc, which correspond to the formula Ia to Ik, Iaa to Ika, Iab to Ikb and Iaab to Ikab, but in which additionally $R^4$ is cyclohexylmethyl.

Especially preferred are compounds of the part-formula:

I* and Ia* to Ik*, which correspond to the formulae I and Ia to Ik, as well as those compounds which correspond to the other abovementioned part-formulae but in which additionally
$R^5$ is (H, OH);

I' and Ia' to Ik', which correspond to the formula I and Ia to Ik, as well as those compounds which correspond to the other abovementioned part-formulae but in which additionally Z is —$CH_2$—NHCONH—A or —$CH_2$—NH—$SO_2$—A.

A particularly preferred group of compounds corresponds to the formula I in which
X is 4-BOC-aminopiperidinocarbonyl or 4-aminopiperidinocarbonyl,
$R^1$, $R^3$ and $R^7$ are each H,
$R^2$ is benzyl,
$R^4$ is cyclohexylmethyl,
$R^5$ is (H, OH),
$R^6$ is H or A,
Z is —$CH_2NHSO_2$—A, —$CH_2NHCONHR^{14}$ or —$CH_2NHCOA$, and
$R^{14}$ is H or A.

The compounds of the formula I, as well as the starting materials for the preparation thereof, are furthermore prepared by methods which are known per se and as are described in the literature (for example in the standard works such as Houben-Weyl, Methoden der organischen Chemie (Methods of Organic Chemistry), published by Georg Thieme, Stuttgart; as well as EP-A 45664, EP-A 77028, EP-A 77029, EP-A 81783, EP-A 249096), specifically under reaction conditions which are known and suitable for the said reactions. In this connection it is also possible to make use of variants which are known per se and which are not mentioned in detail herein.

It is also possible, if desired, to form the starting materials in situ so that they are not isolated from the reaction mixture but are immediately reacted further to give the compounds of the formula I.

The compounds of the formula I can be obtained by liberating them from their functional derivatives by solvolysis, in particular hydrolysis, or by hydrogenolysis.

Preferred starting materials for the solvolysis or hydrogenolysis are those which correspond to the formula I apart from containing, in place of one or more free amino and/or hydroxyl groups, corresponding protected amino and/or hydroxyl groups, preferably those which carry an amino protective group in place of an H atom bonded to an N atom, for example those which correspond to the formula I but contain in place of an His group an N(im)—R'—His group (in which R' is an amino protective group, for example BOM or DNP), or those of the formula X—O—$CR^1R^2$—CO—Y—$NR^3$—$CHR^4$—CH(NHR')—$CH_2$—$CR^6R^7$—Z.

Further preferred starting materials are those which carry, in place of the H atom of a hydroxyl group, a hydroxyl protective group, for example those of the formula Z—O—$CR^1R^2$—CO—Y—$NR^3$—$CHR^4$—CHOR"—$CH_2$—$CR^6R^7$—Z, in which R" is a hydroxyl protective group.

It is also possible for more than one—identical or different—protected amino and/or hydroxyl groups to be present in the molecule of the starting material. If the protective groups which are present differ from one another it is possible in many cases to eliminate them selectively.

The term "amino protective group" is generally known and relates to groups which are suitable for protecting (blocking) an amino group from chemical reactions but which can easily be removed after the desired chemical reaction has been carried out elsewhere in the molecule. Typical of such groups are, in particular, unsubstituted or substituted acyl, aryl (for example DNP), aralkoxymethyl (for example BOM) or aralkyl groups (for example benzyl, 4-nitrobenzyl, triphenylmethyl). Since the amino protective groups are removed after the desired reaction (or reaction sequence), their nature and size are not otherwise critical; however, those which are preferred have 1-20, in particular 1—8, C atoms. The term "acyl group" in connection with the present process is to be interpreted in the widest sense. It embraces acyl groups derived from aliphatic, araliphatic, aromatic or heterocyclic carboxylic acids or sulfonic acids, as well as, in particular, alkoxycarbonyl, aryloxycarbonyl and, especially, aralkoxycarbonyl groups. Examples of such acyl groups are alkanoyl such as acetyl, propionyl, butyryl; aralkanoyl such as phenylacetyl; aroyl such as benzoyl or toluyl; aryloxyalkanoyl such as POA; alkoxycarbonyl such as methoxycarbonyl, ETOC, 2,2,2-trichloroethoxycarbonyl, IPOC, BOC, 2-iodoethoxycarbonyl; aralkyloxycarbonyl such as CBZ, 4-methoxybenzyloxycarbonyl, FMOC. Preferred amino protective groups are BOC, DNP and BOM, as well as CBZ, FMOC, benzyl and acetyl.

The term "hydroxy protective group" is likewise generally known and relates to groups which are suitable for protecting a hydroxyl group from chemical reactions but which can easily be removed after the desired chemical reaction has been carried out elsewhere in the molecule. Typical of such groups are the abovementioned unsubstituted or substituted aryl, aralkyl or acyl groups, as well as alkyl groups. The nature and size of the hydroxyl protective groups are not critical because they are removed again after the desired chemical reaction or reaction sequence; preferred groups have 1-20, especially 1-10, C atoms. Examples of hydroxyl protective groups are, inter alia, tert.-butyl, benzyl, p-nitrobenzoyl, p-toluenesulfonyl and acetyl, with benzyl and acetyl being particularly preferred.

The functional derivatives of the compounds of the formula I which are to be used as starting materials can be prepared by customary methods of amino acid and peptide synthesis as are described, for example, in the said standard works and patent applications, for example also by the solid-phase method of Merrifield.

The liberation of the compounds of the formula I from their functional derivatives is effected—depending on the protective group used—for example with strong acids, preferably with trifluoroacetic acid or perchloric acid, but also with other strong inorganic acids such as hydrochloric acid or sulfuric acid, strong organic carboxylic acids such as trichloroacetic acid or sulfonic acids such as benzene- or p-toluenesulfonic acid. The presence of an additional inert solvent is possible but not always necessary. Suitable and preferred inert solvents are organic, for example carboxylic acids such as acetic acid, ethers such as tetrahydrofuran or dioxane, amides such as dimethylformamide (DMF), halogenated hydrocarbons such as dichloromethane, as well as alcohols such as methanol, ethanol or isopropanol, and water. Furthermore suitable are mixtures of the abovementioned solvents. Trifluoroacetic acid is preferably used in excess without the addition of another solvent, and perchloric acid in the form of a mixture of acetic acid and 70% perchloric acid in the ratio 9:1. The reaction temperatures for the cleavage are preferably between about 0° and about 50°, preferably between 15° and 30° (room temperature).

The BOC group can be eliminated, for example, preferably with 40% trifluoroacetic acid in dichloromethane or with about 3 to 5 N HCl in dioxane at 15°-30°, and the FMOC group with an approximately 5-20% solution of dimethylamine, diethylamine or piperidine in DMF at 15°-30°. Elimination of the DNO group is effected, for example, also with an approximately 3-10% solution of 2-mercaptoethanol in DMF/water at 15°-30°.

Protective groups which can be removed by hydrogenolysis (for example BOM, CBZ or benzyl) can be eliminated, for example by treatment with hydrogen in the presence of a catalyst (for example a noble metal catalyst such as palladium, preferably on a support such as carbon). Solvents suitable for this are those mentioned above, especially, for example, alcohols such as methanol or ethanol or amides such as DMF. Hydrogenolysis is, as a rule, carried out at temperatures between about 0° and 100° under pressures between 1 and 200 bar, preferably at 20°-30° and under 1-10 bar. Hydrogenolysis of the CBZ group is effected satisfactorily, for example, on 5-10% Pd-C in methanol at 20°-30°.

Compounds of the formula I can also be obtained by direct condensation (peptide synthesis) from a carboxylic acid component (formula II) and a hydroxy or amino component (formula III). Examples of suitable carboxylic acid components are those of the part-formulae (a) X—OH, (b) X—O—CR$^1$R$^2$—COOH or (c) X—O—CR$^1$R$^2$—CO—Y—OH, and of hydroxyl or amino components are those of the part-formulae (a) HO—CR$^1$R$^2$—CO—Y—NR$^3$—CHR$^4$CH$^5$—CH$_2$—CR$^6$R$^7$—Z, (b) H—Y—NR$^3$—CHR$^4$—CR$^5$—CH$_2$—CR$^6$R$^7$—Z or (c) H—NR$^3$—CHR$^4$—CR$^5$—CH$_2$—CR$^6$R$^7$—A. The methods preferably used for this are those customary in peptide synthesis, as are described, for example, in Houben-Weyl, l.c., Volume 15/II, pages 1-806 (1974); those methods can also be used for the condensation according to (a), an ester linkage being formed.

The reaction is preferably effected in the presence of a dehydrating agent, for example a carbodiimide such as DCCI or dimethylaminopropylethylcarbodiimide, or else propanephosphinic anhydride (compare Angew. Chem. 92, 129 (1980)), diphenylphosphoryl azide or 2-ethoxy-N-ethoxycarbonyl-1,2-dihydroquinoline, in an inert solvent, for example a halogenated hydrocarbon such as dichloromethane, an ether such as THF or dioxane, an amide such as DMF or dimethylacetamide, or a nitrile such as acetonitrile, at temperatures between about −10° and 40°, preferably between 0° and 30°.

It is also possible, in place of II or III, to use suitable reactive derivatives of these substances in the reaction, for example those in which reactive groups have undergone intermediate blocking with protective groups. The acid derivatives II can be used, for example, in the form of their activated esters which are preferably formed in situ, for example by addition of HOBt or N-hydroxysuccinimide.

The starting materials of the formulae II and III are mostly known. Those which are unknown can be prepared by known methods, for example the abovementioned methods of condensation and of elimination of protective groups.

If desired, it is possible for a functionally modified amino and/or hydroxyl group in a compound of the formula I to be liberated by solvolysis or hydrogenolysis by one of the methods described above.

Thus, for example, a compound of the formula I which contains an $R^{15}$—$C_xH_{2x}$—O—CO—NH—, an AcNH—, an $ArCH_2$—$SO_3$— or an ACCO— group can be converted into the corresponding compound of the formula I which contains in its stead an $H_2N$—, and $HSO_3$— or an HOOC— group, preferably by selective solvolysis by one of the methods indicated above. AOOC— groups can be hydrolyzed, for example, with NaOH or KOH in water/dioxane at temperatures between 0° and 40°, preferably 10° and 30°.

It is also possible to acylate a compound of the formula I which contains a free primary or secondary amino group. Thus, in particular, compounds of the formula I in which Z is a $CH_2$—NH—$R^{12}$ group can be reacted with acrylating agents of the formulae $R^{14}$—$SO_2Cl$, $R^{14}$—COCl or $R^{14}$—NCO, preferably in the presence of an inert solvent such as THF and/or of a base such as pyridine or triethylamine at temperatures between −10° and +30°.

Furthermore, for example, keto compounds of the formula I ($R^5$=O) can be reduced to compounds of the formula I($R^5$=(H, OH)), for example with a complex metal hydride such as $NaBH_4$ which does not simultaneously reduce the peptide carbonyl groups, in an inert solvent such as methanol at temperatures between −10° and +30°.

Keto compounds of the formula I ($R^5$=O) can also be converted into compounds of the formula I ($R^5$=H, $NH_2$) by reductive amination. The reductive amination can be carried out in one or more stages. Thus, for example, the keto compound can be treated with ammonium salts, for example ammonium acetate and $NaCNBH_3$, preferably in an inert solvent, for example an alcohol such as methanol, at temperatures between about 0° and 50°, in particular between 15° and 30°. It is furthermore possible initially to convert the keto compound into the oxime, using hydroxylamine in a customary manner, and to reduce the oxime to the amine, for example by catalytic hydrogenation on Raney nickel.

A base of the formula I can be converted into the relevant acid addition salt using an acid. Particularly suitable acids for this reaction are those which provide physiologically acceptable salts, thus it is possible to use inorganic acids, for example sulfuric acid, nitric acid, hydrohalic acids such as hydrochloric acid or hydrobromic acid, phosphoric acids such as orthophosphoric acid, sulfamic acid, as well as organic acids, in particular aliphatic, alicyclic, araliphatic, aromatic or heterocyclic mono- or polybasic carboxylic, sulfonic or sulfuric acids, for example formic acid, acetic acid, trifluoroacetic acid, propionic acid, pivalic acid, diethylacetic acid, malonic acid, succinic acid, pimelic acid, fumaric acid, maleic acid, lactic acid, tartaric acid, malic acid, citric acid, gluconic acid, ascorbic acid, nicotinic acid, isonicotinic acid, methane- or ethanesulfonic acid, ethanedisulfonic acid, 2-hydroxyethanesulfonic acid, benzenesulfonic acid, p-toluenesulfonic acid, naphthalene-mono- and -disulfonic acids and lauryl sulfuric acid. Salts with physiologically unacceptable acids, for example picrates, can be used to isolate and/or purify the compounds of the formula I.

The new compounds of the formula I and the physiologically acceptable salts thereof can be used to prepare pharmaceutical products by converting them, together with at least one vehicle or auxiliary and, if desired, together with one or more other active compound(s), into a suitable dosage form. The compositions obtained in this way can be used as medicaments in human or veterinary medicine. Suitable vehicles are organic or inorganic substances which are suitable for enteral (for example oral or rectal) or parenteral administration or for administration in the form of a spray for inhalation and which do not react with the new compounds, for example water, vegetable oils, benzyl alcohols, polyethylene glycols, glycerol triacetate and other fatty acid glycerides, gelatine, soya lecithin, carbohydrates such as lactose or starch, magnesium stearate, talc and cellulose. Used orally are, in particular, tablets, coated tablets, capsules, syrups, elixirs or drops; specifically of interest are lacquered tablets and capsules with enteric coatings or capsule shells. Used rectally are suppositories, and for parenteral administration are solutions, preferably oily or aqueous solutions as well as suspensions, emulsions or implants. For administration by spray for inhalation, it is possible to use sprays which contain the active substance either dissolved or suspended in a propellant gas mixture (for example chlorofluorohydrocarbons). The active substance is preferably used for this in micronized form, with one or more additional physiologically tolerated solvents possibly being present, for example ethanol. Solutions for inhalation can be administered with the aid of customary inhalers. The new compounds can also be freeze-dried and the resulting lyophilizates used, for example, to prepare products for injection. The stated compositions can be sterilize and/or contain auxiliaries such as preservatives, stabilizers and/or wetting agents, emulsifiers, salts to influence the osmotic pressure, buffer substances, colorants and/or flavorings. They can, if desired, also contain one or more other active substances, for example one or more vitamins.

The substances according to the invention are, as a rule, administered in analogy to other known, commercially available peptides, but especially in analog to the compounds described in EP-A 249,096, preferably dosages of about 10 mg–10 g, in particular 50–500 mg, per dosage unit. The daily dosage is preferably about 0.2–200 mg/kg, in particular 1–10 mg/kg, of body weight. The specific dose for each particular patient depends, however, on a wide variety of factors, for example on the activity of the specific compound used, on the age, body weight, general state of health and sex, on the diet, on the time and route of administration and on the rate of excretion, medicinal substance combination and severity of the particular disease for which the therapy is applied. Parenteral administration is preferred.

Renin-dependent hypertension and hyperaldosteronism can be effectively treated by administration of dosages of, in particular, about 1–200, preferably 5–50, mg/kg of body weight. For diagnostic purposes, it is possible and preferable for the new compounds to be administered in single doses, particularly about 0.1–10 mg/kg of body weight.

Without further elaboration, it is believed that one skilled in the art can, using the preceding description, utilize the present invention to its fullest extent. The following prepared specific embodiments are, therefore, to be construed as merely illustrative, and not limitative of the remainder of the disclosure in any way whatsoever.

In the foregoing and in the following examples, all temperatures are set forth uncorrected in degrees Celsius and unless otherwise indicated, all parts and percentages are by weight.

The entire disclosures of all applications, patents and publications, cited above and below, and of corresponding application Federal Republic of German P 40 08 403.5, filed Mar. 16, 1990, are hereby incorporated by reference.

EXAMPLES

In the examples which follow, "usual working up" means: if necessary, water is added, and pH is adjusted to between 2 and 8, depending on the constitution of the final product, extraction is carried out with ethyl acetate or dichloromethane, the organic phase is separated off, dried over sodium sulfate and concentrated, and purification is carried out by chromatography on silica gel and/or crystallization.

TFA = trifluoroacetate.

EXAMPLE 1

1 g of N-ethyl-N'-[4S-hydroxy-5S-(4-tert.-butoxycarbonylaminopiperidinocarbonyloxy)-3-phenylpropionyl-L-(N-(imi)-benzyloxymethylhistidyl)amino)-6-cyclohexylhexyl]urea [=N-ethyl-N'-[4S-hydroxy-5S-(4-BOC-aminopiperidinocarbonyl-Pla-(imi-BOM-His-)amino)-6-cyclohexylhexyl]urea, m.p. 99°-100°; obtainable by elimination of the BOC group from N-ethyl-N'-[4S-hydroxy-5S-(BOC-(imi-BOM-His)amino)-6-cyclohexylhexyl]urea (m.p. 75°-76°) and condensation with 4-BOC-aminopiperidinocarbonyloxy-Pla-Oh which, in its turn, can be obtained by reaction of methyl 2S-hydroxy-3-phenylpropionate ("Pla-OMe") with phosgene in boiling toluene and reaction of the resulting methyl 2S-chlorocarbonyloxy-3-phenylpropionate with 4-BOC-aminopiperidine in THF in the presence of triethylamine] is dissolved in 25 ml of ethanol, hydrogenated on 0.5 g of 10% Pd-C at 20° and under 1 bar until H₂ uptake ceases, filtered and evaporated, and purification by chromatography gives N-ethyl-N'-[4S-hydroxy-5S-(4-BOC-aminopiperidinocarbonyl-Pla-His-amino)-6-cyclohexylhexyl]urea, m.p. 180° (decomposition).

The following are obtained analogously by hydrogenolysis of the corresponding imi-BOM-His derivatives:

N-[4S-Hydroxy-5S-(4-BOC-aminopiperidinocarbonyl-Ola-His-amino)-6-cyclohexylhexyl]urea, m.p. 196°-197°
N-Isopropyl-N'-[4S-hydroxy-5S-(4-BOC-aminopiperidinocarbonyl-Pla-His-amino)-6-cyclohexylhexyl]urea, m.p. 176°-177°
N-[2R-Methyl-4S-hydroxy-5S-(4-BOC-aminopiperidinocarbonyl-Pla-His-amino)-6-cyclohexylhexyl]urea
N-Ethyl-N'-[2R-methyl-4S-hydroxy-5S-(4-BOC-aminopiperidinocarbonyl-Pla-His-amino)-6-cyclohexylhexyl]urea,
N-Isopropyl-N'-[2R-methyl-4S-hydroxy-5S-(4-BOC-aminopiperidinocarbonyl-Pla-His-amino)-6-cyclohexylhexyl]urea, m.p. 200°-201° [from N-isopropyl-N'-(2R-methyl-4S-hydroxy-5S-BOC-(imi-BOM-His)-amino-6-cyclohexylhexyl)urea (m.p. 146°-147°) via N-isopropyl-N'-[2R-methyl-4S-hydroxy-5S-(4-BOC-aminopiperidinocarbonyl-Pla(imi-BOM-His)-amino)-6-cyclohexylhexyl]urea (m.p. 120°-121°)]
N-[2S-Isopropyl-4S-hydroxy-5S-(4-BOC-aminopiperidinocarbonyl-Pla-His-amino)-6-cyclohexylhexyl]urea
N-Ethyl-N'-[2S-isopropyl-4S-hydroxy-5S-(4-BOC-aminopiperidinocarbonyl-Pla-His-amino)-6-cyclohexylhexyl]urea, [from N-ethyl-N'-(2S-isopropyl-4S-hydroxy-5S-BOC-amino-6-cyclohexylhexyl)urea (m.p. 144°-145°) via N-ethyl N'-[2S-isopropyl-4S-hydroxy-5S-BOC-(imi-BOM-His)-amino-6-cyclohexylhexyl]urea (m.p. 75°-76°) and N-ethyl-N'-[2S-isopropyl-4S-hydroxy-5S-(4-BOC-aminopiperidinocarbonyl-Pla-(imi-BOM-His)-amino)-6-cyclohexylhexyl]urea, m.p. 106°-107°
N-Isopropyl-N'-[2S-isopropyl-4S-hydroxy-5S-hydroxy-5S-(4-BOC-aminopiperidinocarbonyl-Pla-His-amino)-6-cyclohexylhexyl]urea N-Ethyl-N'-[4S-hydroxy-5S-(2S-(4-BOC-aminopiperidinocarbonyloxy)-4-methylbutyryl-His-amino)-6-cyclohexylhexyl]urea
N-Ethyl-N'-[2S-isopropyl-4S-hydroxy-5S-(2S-(4-BOC-aminopiperidinocarbonyloxy)-4-methylbutyryl-His-amino)-6-cyclohexylhexyl]urea
N-Ethyl-N'-[4S-hydroxy-5S-(2S-(4-BOC-aminopiperidinocarbonyloxy)hexanoyl-His-amino)-6-cyclohexylhexyl]urea
N-Ethyl-N'-[2S-isopropyl-4S-hydroxy-5S-(2S-(4-BOC-aminopiperidinocarbonyloxy)hexanoyl-His-amino)-6-cyclohexylhexyl]urea
N-Ethyl-N'-[4S-hydroxy-5S-(2S-(4-BOC-aminopiperidinocarbonyloxy)-3-cyclohexylpropionyl-His-amino)-6-cyclohexylhexyl]urea
N-Ethyl-N'-[2S-isopropyl-4S-hydroxy-5S-(2S-(4-BOC-aminopiperidinocarbonyloxy)-3-cyclohexylpropionyl-His-amino)-6-cyclohexylhexyl]urea
N-Ethyl-N'-[4S-hydroxy-5S-(2S-(4-BOC-aminopiperidinocarbonyloxy-3-p-methoxyphenylpropionyl-His-amino)-6-cyclohexylhexyl]urea
N-Ethyl-N'-[2S-isopropyl-4S-hydroxy-5S-(2S-(4-BOC-aminopiperidinocarbonyloxy)-3-p-methoxyphenylpropionyl-His-amino)-6-cyclohexylhexyl]urea
N-Ethyl-N'-[4S-hydroxy-5S-(2S-(4-BOC-aminopiperidinocarbonyloxy)- 3-(2-thienyl)propionyl-His-amino)-6-cyclohexylhexyl]urea
N-Ethyl-N'-[2S-isopropyl-4S-hydroxy-5S-(2S-(4-BOC-aminopiperidinocarbonyloxy)-3-(2-thienyl)propionyl-His-amino)-6-cyclohexylhexyl]urea
N-[4S-Hydroxy-5S-(4-BOC-aminopiperidinocarbonyl-Pla-His-amino)-6-cyclohexylhexyl]propanesulfonamide, m.p. 164°-165√
N-[2R-Methyl-4S-hydroxy-5S-(4-BOC-aminopiperidinocarbonyl-Pla-His-amino)-6-cyclohexylhexyl]propanesulfonamide, m.p. 116°-117° [from N-(2R-methyl-4S-hydroxy-5S-BOC-(imii-BOM-His)-amino-6-cyclohexylhexyl)propanesulfonamide (m.p. 147°-148°) via N-[2R-methyl-4S-hydroxy-5S-(4-BOC-aminopiperidinocarbonyl-Pla-(imi-BOM-His) -amino)-6-cyclohexylhexyl]propanesulfonamide (m.p. 90°-91°)]
N-[2S-Isopropyl-4S-hydroxy-5S-(4-BOC-aminopiperidinocarbonyl-Pla-His-amino)-6-cyclyhexylhexyl]propanesulfonamide, [from N-(2S-isopropyl-4S-hydroxy-5S-BOC-amino-6-cyclohexylhexyl)-propanesulfonamide (oil) via N-(2S-isopropyl-4S-hydroxy-5S-BOC-(imi-BOM-His)-amino-6-cyclohexylhexyl)propanesulfonamide (m.p. 101°-102°)]
N- [4S-Hydroxy-5S-(4-BOC-aminopiperidinocarbonyl-Pla-His-amino)-7-methyloctyl]propanesulfonamide
N-[2R-Methyl-4S-hydroxy-5S-(4-BOC-aminopiperidinocarbonyl-Pla-His-amino)-7-methyloctyl]propanesulfonamide
N-[2S-Isopropyl-4S-hydroxy-5S-(4-BOC-aminopiperidinocarbonyl-Pla-His-amino)-7-methyloctyl]propanesulfonamide
N-[4S-Hydroxy-5S-(4-BOC-aminopiperidinocarbonyl-Pla-His-amino)-6-phenylhexyl]propanesulfonamide N-[2R-Methyl-4S-hydroxy-5S-(4-BOC-aminopiperidinocarbonyl-Pla-His-amino)-6-phenylhexyl]propanesulfonamide
N-[2S-Isopropyl-4S-hydroxy-5S-(4-BOC-aminopiperidinocarbonyl-Pla-His-amino)-6-phenylhexyl]propanesulfonamide
N-[4S-Hydroxy-5S-(4-BOC-aminopiperidinocarbonyl-Pla-His-amino)-6-cyclohexylhexyl]isovaleramide, m.p. 176°-177° [from N-3-(3-BOC-4-cyclohexylmethyl-2,2-dimethyl-5-oxazolidinyl)propylisovaleramide (oil) via N-[4S-hydroxy-5-BOC-(imi-BOM-His)-amino-6-cyclohexylhexyl]isovaleramide (m.p. 135°-136°) and N-(4S-hydroxy-5S-(4-BOC-aminopiperidinocarbonyl-Pla-(imi-BOM-His)-amino-6-cyclohexylhexyl]isovaleramide (m.p. 93°-94°)].

EXAMPLE 2

A mixture of 1.011 mg of N-[2R-methyl-4S-hydroxy-5S-(2S-(4-BOC-aminopiperidinocarbonyloxy)-3-phenylpropionyl-L-(N-(imi)-2,4-dinitrophenylhistidyl)-amino)-6-cyclohexylhexyl]propanesulfonamide [=N-[2R-methyl-4S-hydroxy-5S-(4-BOC-aminopiperidinocarbonyl-Pla-(imi-DNP-His)-amino)-6-cyclohexylhexyl]propanesulfonamide; obtainable by condensation of 4-BOC-aminopiperidinocarbonyl-Pla-OH with N-(2R-methyl-4S-hydroxy-5S-(H-(imi-DNP-His)-amino)-6-cyclohexylhexyl]propanesulfonamide in analogy to Example 3], 2 g of 2-mercaptoethanol, 20 ml of DMF and 20 ml of water is adjusted to pH 8, while stirring at 20°, with aqueous $Na_2CO_3$ solution and is stirred at 20° for a further 2 h. The usual working up results in N-[2R-methyl-4S-hydroxy-5S-(4-BOC-aminopiperidinocarbonyl-Pla-His-amino)-6-cyclohexylhexyl]propanesulfonamide, m.p. 116°-117°.

The other compounds indicated in Example 1 are obtained analogously from the corresponding imi-DNP-His derivatives.

EXAMPLE 3

In analogy to Example 1, hydrogenolysis of 1-CBZ-amino-4S-hydroxy-5S-(4-BOC-aminopiperidinocarbonylamino-Pla-His-amino)-6-cyclohexylhexane [obtainable by reaction of 1-CBZ-amino-4S-hydroxy-5S-amino-6-cyclohexylhexane with 4-BOC-aminopiperidinocarbonylamino-Phe-(imi-DNP-His)-OH and subsequent elimination of the DNP group in analogy to Example 2] results in 1-amino-4S-hydroxy-5S-(4-BOC-aminopiperidinocarbonylamino-Pla-His-amino)-6-cyclohexylhexane.

EXAMPLE 4

1.01 g of N-methylmorpholine are added to a solution of 4.02 g of N-ethyl-N'-[4S-hydroxy-5S-(H-(S-Me-Cys)-amino)-6-cyclohexylhexyl]urea [obtainable from N-ethyl-N'-3-(2,2-dimethyl-3-BOC-4-cyclohexylmethyl-5-oxazolidinyl)propylurea (m.p. 105°-106°) via N-ethyl-N'-(4S-hydroxy-5S-amino-6-cyclohexylhexyl)urea and N-ethyl-N'-(4S-hydroxy-5S-BOC-(S-Me-Cys)-amino-6-cyclohexylhexyl)urea (m.p. 144°-145°)] in 60 ml of dichloromethane. While stirring, 3.92 g of O-(4-BOC-aminopiperidinocarbonyl)-Pla-OH, 1.35 g of HOBt and a solution of 2.06 g of DCCI in 60 ml of dichloromethane are added, the mixture is stirred at 2°-4° for 14 h, the precipitated dicyclohexylurea is filtered off, and the filtrate is evaporated. The usual working up results in N-ethyl-N-'-[4S-hydroxy-5S-(4-BOC-aminopiperidinocarbonyl-Pla-(S-Me-Cys)-amino)-6-cyclohexylhexyl]urea, m.p. 172°-173°.

The following are obtained analogously
N-Ethyl-N'-[4S-hydroxy-5S-(pyrrolidinocarbonyl-Pla-(S-Me-Cys)-amino)-6-cyclohexylhexyl]urea
N-Ethyl-N'-[4S-hydroxy-5S-(piperidinocarbonyl-Pla-(S-Me-Cys)-amino)-6-cyclohexylhexyl]urea
N-Ethyl-N'-[4S-hydroxy-5S-(morpholinocarbonyl-Pla-(S-Me-Cys)-amino)-6-cyclohexylhexyl]urea, m.p. 137° (dec.)
N-Ethyl-N'-[4S-hydroxy-5S-(4-ethoxycarbonyl-piperidinocarbonyl-Pla-(S-Me-Cys)-amino)-6-cyclohexylhexyl]urea
N-Ethyl-N'-[4S-hydroxy-5S-(dimethylaminopiperidinocarbonyl-Pla-(S-Me-Cys)-amino)-6-cyclohexylhexyl]urea
N-Ethyl-N'-[4S-hydroxy-5S-(4-N-BOC-N-methylaminopiperidinocarbonyl-Pla-(S-Me-Cys)-amino)-6-cyclohexylhexyl]urea
N-Ethyl-N'-[4S-hydroxy-5S-(isobutyl-Pla-(S-Me-Cys)-amino)-6-cyclohexylhexyl]urea
N-Ethyl-N'-[4S-hydroxy-5S-(tert.-butoxycarbonyl-Pla-(S-Me-Cys)-amino)-6-cyclohexylhexyl]urea
N-Ethyl-N'-[4S-hydroxy-5S-(benzyloxycarbonyl-Pla-(S-Me-Cys)-amino)-6-cyclohexylhexyl]urea
N-Ethyl-N'-[4S-hydroxy-5S-(4-BOC-aminopipiperidinocarbonyl-Pla-(S-Me-Cys)-amino)-6-cyclohexylhexyl]urea
N-[4S-Hydroxy-5S-(4-BOC-aminopiperidinocarbonyl-Pla-(S-Me-Cys)-amino)-6-cyclohexylhexyl]urea
N-Isopropyl-N'-[4S-hydroxy-5S-(4-BOC-aminopiperidinocarbonyl-Pla-(S-Me-Cys)-amino)-6-cyclohexylhexyl]urea
N-[2R-Methyl-4S-hydroxy-5S-(4-BOC-aminopiperidinocarbonyl-Pla-(S-Me-Cys)-amino)-6-cyclohexylhexyl]urea
N-Ethyl-N'-[2R-methyl-4S-hydroxy-5S-(4-BOC-aminopiperidinocarbonyl-Pla-(S-Me-Cys)-amino)-6-cyclohexylhexyl]urea
N-Isopropyl-N'-[2R-methyl-4S-hydroxy-5S-(4-BOC-aminopiperidinocarbonyl-Pla-(S-Me-Cys)-amino)-
N-[2S-Isopropyl-4S-hydroxy-5S-(4-BOC-aminopiperidinocarbonyl-Pla-(S-Me-Cys)-amino)-6-cyclohexylhexyl]urea
N-Ethyl-N'-[2S-isopropyl-4S-hydroxy-5S-(4-BOC-aminopiperidinocarbonyl-Pla-(S-Me-Cys)-amino)-6-cyclohexylhexyl]urea, m.p. 115°-116° [from N-ethyl-N'-(2S-isopropyl-4S-hydroxy-5S-BOC-amino-6-cyclohexylhexyl)urea (m.p. 144°-145°) via N-ethyl-N'-(2S-isopropyl-4S-hydroxy-5S-BOC-(N-Me-Cys)-amino-6-cyclohexylhexyl)urea (m.p. 89°-90°)]
N-Isopropyl-N'-[2S-isopropyl-4S-hydroxy-5S-(4-BOC-aminopiperidinocarbonyl-Pla-(S-Me-Cys)-amino)-6-cyclohexylhexyl]urea
N-[4S-Hydroxy-5S-(4-BOC-aminopiperidinocarbonyl-Pla-(S-Me-Cys)-amino)-7-methyloctyl]urea
N-Ethyl-N'-[4S-hydroxy-5S-(4-BOC-aminopiperidinocarbonyl-Pla-(S-Me-Cys)-amino)-7-methyloctyl]urea
N-Isopropyl-N'-[4S-hydroxy-5S-(4-BOC-aminopiperidinocarbonyl-Pla-(S-Me-Cys)-amino)-7-methyloctyl]urea
N-Ethyl-N'-[4S-hydroxy-5S-(morpholinocarbonyl-Pla-amino-6-cyclohexylhexyl]urea
N-Ethyl-N'-[4S-hydroxy-5S-(4-BOC-aminopiperidinocarbonyl-Pla-amino)-6-cyclohexylhexyl]urea
N-Ethyl-N'-[2R-methyl-4S-hydroxy-5S-(4-BOC-aminopiperidinocarbonyl-Pla-amino)-6-cyclohexylhexyl]urea N-Ethyl-N'-[2S-isopropyl-4S-hydroxy-5S-(4-BOC-aminopiperidinocarbonyl-Pla-amino)-6-cyclohexylhexyl]urea, m.p. 163°–164°
N-[4S-Hydroxy-5S-(4-BOC-aminopiperidinocarbonyl-Pla-(S-Me-Cys)-amino)-6-cyclohexylhexyl]propanesulfonamide  N-[2R-Methyl-4S-hydroxy-5S-(4BOC-aminopiperidinocarbonyl-Pla-(S-Me-Cys)-amino)-6-cyclohexylhexyl]propanesulfonamide
N-[2S-Isopropyl-4S-hydroxy-5S-(4-BOC-aminopiperidinocarbonyl-Pla-(S-Me-Cys)-amino)-6-cyclohexylhexyl]propanesulfonamide
N-[4S-Hydroxy-5S-(4BOC-aminopiperidinocarbonyl-Pla-(S-Me-Cys)-amino)-6-cyclohexylhexyl]butyramide
N-[4S-Hydroxy-5S-(4-BOC-aminopiperidinocarbonyl-Pla-(S-Me-Cys)-amino)-6-cyclohexylhexyl]isovaleramide
N-[4S-Hydroxy-5S-(4-BOC-aminopiperidinocarbonyl-Pla-(S-Me-Cys)-amino)-6-cyclohexylhexyl]benzamide
N-[4S-Hydroxy-5S-(4-BOC-aminopiperidinocarbonyl-Pla-(S-Me-Cys)-amino)-6-cyclohexylhexyl]picolinamide
N-Ethyl-N'-[4S-hydroxy-5S-(4-BOC-aminopiperidinocarbonyl-Pla-(S-Me-Cys)-amino)-6-cyclohexylhexyl]thiourea.

EXAMPLE 5

In analogy to Example 4, N-ethyl-N'-(2S-isopropyl-4S-hydroxy-5S-(4-BOC-aminopiperidinocarbonyl-Pla-(S-Me-Cys)-amino)-6-cyclohexylhexyl]urea, m.p. 115°–116°, is obtained from 4-BOC-aminopiperidinocarbonyl-Pla-(S-Me-Cys)-OH and N-ethyl-N'-(2S-isopropyl-4S-hydroxy-5S-amino-6-cyclohexylhexyl)urea.

The following are obtained analogously
N-Ethyl-N'-[4S-hydroxy-5S-(4-BOC-aminopiperidinocarbonyl-Pla-βAla-amino)-6-cyclohexylhexyl]urea
N-Ethyl-N'-[4S-hydroxy-5S-(4-BOC-aminopiperidinocarbonyl-Pla-Asn-amino)-6-cyclohexylhexyl]urea
N-Ethyl-N'-[4S-hydroxy-5S-(4-BOC-aminopiperidinocarbonyl-Pla-(N-Me-His)-amino)-6-cyclohexylhexyl]urea
N-Ethyl-N'-[4S-hydroxy-5S-(4-BOC-aminopiperidinocarbonyl-Pla-Leu-amino)-6-cyclohexylhexyl]urea, m.p. 107°–108°
N-Ethyl-N'-[4S-hydroxy-5S-(4-BOC-aminopiperidinocarbonyl-Pla-Met-amino)-6-cyclohexylhexyl]urea
N-Ethyl-N'-[4S-hydroxy-5S-(4-BOC-aminopiperidinocarbonyl-Pla-Nle-amino)-6-cyclohexylhexyl]urea
N-Ethyl-N'-[4S-hydroxy-5S-(4-BOC-aminopiperidinocarbonyl-Pla-Nva-amino)-6-cyclohexylhexyl]urea
N-Ethyl-N'-[4S-hydroxy-5S-(4-BOC-aminopiperidinocarbonyl-Pla-(3-Oya)-amino)-6-cyclohexylhexyl]urea
N-Ethyl-N'-[4S-hydroxy-5S-(4-BOC-aminopiperidinocarbonyl-Pla-(2-Tia)-amino)-6-cyclohexylhexyl]urea
N-Ethyl-N'-[4S-hydroxy-5S-(4-BOC-aminopiperidinocarbonyl-Pla-Val-amino)-6-cyclohexylhexyl]urea

EXAMPLE 6

In analogy to Example 4, N-propyl-N'-[4S-hydroxy-5S-(POA-Pla-βAla-amino)-7-methyloctyl]urea is obtained from phenoxyacetic acid (=POA-OH) and N-propyl-N'-[4S-hydroxy-5S-(H-Pla-βAla-amino)-7-methyloctyl]urea.

EXAMPLE 7

A solution of 1.25 g of cyclohexyl isocyanate in 15 ml of THF is added dropwise at 20° to a stirred solution of 6.89 g of 4S-hydroxy-5S-(4-BOC-aminopiperidinocarbonyl-Pla-Leu-amino)-6-cyclohexylhexylamine in 60 ml of THF. The mixture is stirred at 20° for a further 3 h, and the usual working up results in N-cyclohexyl-N'-[4S-hydroxy-5S-(4-BOC-aminopiperidinocarbonyl-Pla-Leu-amino)-6-cyclohexylhexyl]urea.

EXAMPLE 8

A solution of 1 g of N-ethyl-N'-[4S-hydroxy-5S-(4-BOC-aminopiperidinocarbonyl-Pla-His-amino)-6-cyclohexylhexyl]urea in 20 ml of dichloromethane and 20 ml of trifluoroacetic acid is stirred at 20° for 1 h and then evaporated. This results in N-ethyl-N'-[4S-hydroxy-5S-(4-aminopiperidinocarbonyl-Pla-His-amino)-6-cyclohexylhexyl]urea, Bis-TFA, m.p. 141° (decomposition).

The following are obtained analogously by cleavage of the appropriate BOC derivatives:
N-[4S-Hydroxy-5S-(4-aminopiperidinocarbonyl-Pla-His-amino)-6-cyclohexylhexyl]urea
N-Isopropyl-N'-[4S-hydroxy-5S-(4-aminopiperidinocarbonyl-Pla-His-amino)-6-cyclohexylhexyl]urea
N-[2R-Methyl-4S-hydroxy-5S-(4-aminopiperidinocarbonyl-Pla-His-amino)-6-cyclohexylhexyl]urea
N-Ethyl-N'-[2R-methyl-4S-hydroxy-5S-(4-aminopiperidinocarbonyl-Pla-His-amino)-6-cyclohexylhexyl]urea
N-Isopropyl-N'-[2R-methyl-4S-hydroxy-5S-(4-aminopiperidinocarbonyl-Pla-His-amino)-6-cyclohexylhexyl]urea, Bis-TFA, m.p. 141°
N-[2S-Isopropyl-4S-hydroxy-5S-(4-aminopiperidinocarbonyl-Pla-His-amino)-6-cyclohexylhexyl]urea
N-Ethyl-N'-[2S-isopropyl-4S-hydroxy-5S-(4-aminopiperidinocarbonyl-Pla-His-amino)-6-cyclohexylhexyl]urea, Bis-TFA, m.p. 154°–155°
N-Isopropyl-N'-[2-isopropyl-4S-hydroxy-5S-(4-aminopiperidinocarbonyl-Pla-His-amino)-6-cyclohexylhexyl]urea
N-Ethyl-N'-[4S-hydroxy-5S-(4-aminopiperidinocarbonyl-Pla-βAla-amino)-6-cyclohexylhexyl]urea
N-Ethyl-N'-[4S-hydroxy-5S-(4-aminopiperidinocarbonyl-Pla-Asn-amino)-6-cyclohexylhexyl]urea
N-Ethyl-N'-[4S-hydroxy-5S-(4-aminopiperidinocarbonyl-Pla-(N-Me-His)-amino)-6-cyclohexylhexyl]urea
N-Ethyl-N'-[4S-hydroxy-5S-(4-aminopiperidinocarbonyl-Pla-Leu-amino)-6-cyclohexylhexyl]urea, TFA, m.p. 152°–153°
N-Ethyl-N'-[4S-hydroxy-5S-(4-aminopiperidinocarbonyl-Pla-Met-amino)-6-cyclohexylhexyl]urea
N-Ethyl-N'-[4S-hydroxy-5S-(4-aminopiperidinocarbonyl-Pla-Nle-amino)-6-cyclohexylhexyl]urea
N-Ethyl-N'-[4S-hydroxy-5S-(4-aminopiperidinocarbonyl-Pla-Nva-amino)-6-cyclohexylhexyl]urea
N-Ethyl-N'-[4S-hydroxy-5S-(4-aminopiperidinocarbonyl-Pla-(3-Pya)-amino)-6-cyclohexylhexyl]urea
N-Ethyl-N'-[4S-hydroxy-5S-(4-aminopiperidinocarbonyl-Pla-(2-Tia)-amino)-6-cyclohexylhexyl]urea
N-Ethyl-N'-[4S-hydroxy-5S-(4-aminopiperidinocarbonyl-Pla-Val-amino)-6-cyclohexylhexyl]urea N-[4S-Hydroxy-5S-(4-aminopiperidinocarbonyl-Pla-(S-Me-Cys)-amino-6-cyclohexylhexyl]urea
N-Ethyl-N'-[4S-hydroxy-5S-(4-aminopiperidinocarbonyl-Pla-(S-Me-Cys)-amino)-6-cyclohexylhexyl]urea, TFA, m.p. 113°-114°
N-Isopropyl-N'-[4S-hydroxy-5S-(4-aminopiperidinocarbonyl-Pla-(S-Me-Cys)-amino)-6-cyclohexylhexyl]urea
N-[2R-Methyl-4S-hydroxy-5S-(4-aminopiperidinocarbonyl-Pla-(S-Me-Cys)-amino)-6-cyclohexylhexyl]urea
N-Ethyl-N'-[2R-methyl-4S-hydroxy-5S-(4-aminopiperidinocarbonyl-Pla-(S-Me-Cys)-amino)-6-cyclohexylhexyl]urea
N-Isopropyl-N'-[2R-methyl-4S-hydroxy-5S-(4-aminopiperidinocarbonyl-Pla-(S-Me-Cys)-amino)-6-cyclohexylhexyl]urea
N-[2S-Isopropyl-4S-hydroxy-5S-(4-aminopiperidinocarbonyl-Pla-(S-Me-Cys)-amino)-6-cyclohexylhexyl]urea
N-Ethyl-N'-[2S-isopropyl-4S-hydroxy-5S-(4-aminopiperidinocarbonyl-Pla-(S-Me-Cys)-amino)-6-cyclohexylhexyl]urea, TFA, m.p. 123°-124°
N-Isopropyl-N'-[2S-isopropyl-4S-hydroxy-5S-(4-aminopiperidinocarbonyl-Pla-(S-Me-Cys)-amino)-6-cyclohexylhexyl]urea
N-[4S-Hydroxy-5S-(4-aminopiperidinocarbonyl-Pla-(S-Me-Cys)-amino)-7-methyloctyl]urea
N-Ethyl-N'-[4S-hydroxy-5S-(4-aminopiperidinocarbonyl-Pla-(S-Me-Cys)-amino)-7-methyloctyl]urea
N-Isopropyl-N'-[4S-hydroxy-5S-(4-aminopiperidinocarbonyl-Pla-(S-Me-Cys)-amino)-7-methyloctyl]urea
N-Ethyl-N'[4S-hydroxy-5S-(4-aminopiperidinocarbonyl-Pla-amino)-6-cyclohexylhexyl]urea
N-Ethyl-N'-[2R-methyl-4S-hydroxy-5S-(4-aminopiperidinocarbonyl-Pla-amino)-6-cyclohexylhexyl]urea
N-Ethyl-N'-[2S-isopropyl-4S-hydroxy-5S-(4-aminopiperidinocarbonyl-Pla-amino)-6-cyclohexylhexyl]urea, TFA, m.p. 135°-136°
N-Ethyl-N'-[4S-hydroxy-5S-(4-methylaminopiperidinocarbonyl-Pla-(S-Me-Cys-amino)-6-cyclohexylhexyl]urea
N-Ethyl-N'-[4S-hydroxy-5S-(2S-(4-aminopiperidinocarbonyloxy)-4-methylbutyryl-His-amino)-6-cyclohexylhexyl]urea
N-Ethyl-N'-[2S-isopropyl-4S-hydroxy-5S-(2S-(4-aminopiperidinocarbonyloxy)-4-methylbutyryl-His-amino)-6-cyclohexylhexyl]urea
N-Ethyl-N'-[4S-hydroxy-5S-(2S-(4-aminopiperidinocarbonyloxy)hexanoyl-His-amino)-6-cyclohexylhexyl]urea
N-Ethyl-N'-[2S-isopropyl-4S-hydroxy-5S-(2S-(4-aminopiperidinocarbonyloxy)-hexanoyl-His-amino)-6-cyclohexylhexyl]urea
N-Ethyl-N'-[4S-hydroxy-5S-(2S-(4-aminopiperidinocarbonyloxy)-3-cyclohexylhexylpropionyl-His-amino)-6-cyclohexylhexyl]urea
N-Ethyl-N'-[2S-isopropyl-4S-hydroxy-5S-(2S-(4-aminopipericinocasrbonyloxy)-3-cyclohexylpropionyl-His-amino)-6-cyclohexylhexyl]urea
N-Ethyl-N'-[4-S-hydroxy-5S-(2S-(4-aminopiperidinocarbonyloxy)-3-p-methoxyphenylpropionyl-His-amino)-6-cyclohexylhexyl]urea
N-Ethyl-N'-[2S-isopropyl-4S-hydroxy-5S-(2S-(4-aminopiperidinocarbonyloxy)-3-p-methoxyphenylpropionyl-His-amino)- 6-cyclohexylhexyl]urea
N-Ethyl-N'-[4S-hydroxy-5S-(2S-(4-aminopiperidinocarbonyloxy)-3-(2-thienyl)propionyl-His-amino)-6-cyclohexyl]urea
N-Ethyl-N'-[2S-isopropyl-4S-hydroxy-5S-(2S-(4-aminopiperidinocarbonyloxy)-3-(2-thienyl)propionyl-His-amino)-6-cyclohexylhexyl]urea
N-[4S-hydroxy-5S-(4-aminopiperidinocarbonyl-Pla-His-amino)-6-cyclohexylhexyl]propanesulfonamide
N-[2R-Methyl-4S-hydroxy-5S-(4-aminopiperidinocarbonyl-Pla-His-amino)-6-cyclohexylhexyl]propanesulfonamide, Bis-TFA, m.p. 136° (decomposition)
N-[2S-Isopropyl-4S-hydroxy-5S-(4-aminopiperidinocarbonyl-Pla-His-amino)-6-cyclohexylhexyl]propanesulfonamide, Bis-TFA, m.p. 141°-143°
N[4S-Hydroxy-5S-(4-aminopiperidinocarbonyl-Pla-(S-Me-Cys)-amino)-6-cyclohexylhexyl]propanesulfonamide
N-[2R-Methyl-4S-hydroxy-5S-(4-aminopiperidinocarbonyl-Pla-(S-Me-Cys)-amino)-6-cyclohexylhexyl]-propanesulfonamide
N-[2S-Isopropyl-4S-hydroxy-5S-(4-aminopiperidinocarbonyl-Pla-(S-Me-Cys)-amino)-6-cyclohexylhexyl]propanesulfonamide
N-[4S-Hydroxy-5S-(4-aminopiperidinocarbonyl-Pla-(His-amino)-7-methyloctyl]propanesulfonamide
N-[2R-Methyl-4S-hydroxy-5S-(4-aminopiperidinocarbonyl-Pla-(His-amino)-7-methyloctyl]propanesulfonamide
N-[2S-Isopropyl-4S-hydroxy-5S-(4-aminopiperidinocarbonyl-Pla-(His-amino)-7-methyloctyl]propanesulfonamide
N-[4S-Hydroxy-5S-(4-aminopiperidinocarbonyl-Pla-(His-amino)-6-phenylhexyl]propanesulfonamide
N-[2R-Methyl-4S-hydroxy-5S-(4-aminopiperidinocarbonyl-Pla-(His-amino)-6-phenylhexyl]propanesulfonamide
N-[2S-Isopropyl-4S-hydroxy-5S-(4-aminopiperidinocarbonyl-Pla-(His-amino)-6-phenylhexyl]propanesulfonamide
N-[4S-Hydroxy-5S-(4-aminopiperidinocarbonyl-Pla-His-amino)-6-cyclohexylhexyl]isovaleramide, Bis-TFA, m.p. 122°-123°
N-[4S-Hydroxy-5S-(4-aminopiperidinocarbonyl-Pla-(S-Me-Cys)-amino)- 6-cyclohexylhexyl]butyramide
N-[4S-Hydroxy-5S-(4-aminopiperidinocarbonyl-Pla-(S-Me-Cys)-amino)-6-cyclohexylhexyl]isovaleramide
N-[4S-Hydroxy-5S-(4-aminopiperidinocarbonyl-Pla-(S-Me-Cys)-amino)-6-cyclohexylhexyl]benzamide
N-[4S-Hydroxy-5S-(4-aminopiperidinocarbonyl-Pla-(S-Me-Cys)-amino)-6-cyclohexylhexyl]picolinamide
N-Ethyl-N'-[4S-hydroxy-5S-(4-aminopiperidinocarbonyl-Pla-(S-Me-Cys)-amino)-6-cyclohexylhexyl]thiourea.

EXAMPLE 9

A mixture of 1 g of N-ethyl-N'-[4S-hydroxy-5S-(4-ethoxycarbonylpiperidinocarbonyl-Pla-(S-Me-Cys)-amino)-6-cyclohexylhexyl]urea, 50 ml of dioxane and 20 ml of 2N aqueous NaOH solution is stirred at 20° for 3 h. The usual working up results in N-ethyl-N'-[4S-hydroxy-5S-(4-carboxypiperidinocarbonyl-Pla-(S-Me-Cys)-amino)-6-cyclohexylhexyl]urea.

EXAMPLE 10

1.01 g of triethylamine are added, followed by a solution of 1.15 g of methanesulfonyl chloride in 10 ml of THF dropwise while stirring at 0°, to a solution of 6.89 g of 4S-hydroxy-5S-(4-BOC-aminopiperidinocarbonyl- Pla-Leu-amino)-6-cyclohexylhexylamine in 250 ml of THF. The mixture is then stirred for 1 h, during which the temperature is allowed to rise to 20°, and the usual working up results in N-[4S-hydroxy-5S-(4-BOC-aminopiperidinocarbonyl-Pla-Leu-amino)-6-cyclohexylhexyl]methanesulfonamide.

EXAMPLE 11

In analogy to Example 1, N-ethyl-N'-[4S-hydroxy-5S-(4-aminopiperidinocarbonyl-Pla-(S-Me-Cys)-amino)-6-cyclohexylhexyl]urea, TFA, m.p. 123°–124°, is obtained from N-ethyl-N'-[4S-hydroxy-5S-(4-CBZ-aminopiperidinocarbonyl-Pla-(S-Me-Cys)-amino)-6-cyclohexylhexyl]urea.

EXAMPLE 12

In analogy to Example 4, N-[2S-isopropyl-4-oxo-5S-(4-dimethylaminobutyryl-Pla-Gly-amino)-6-cyclohexylhexyl]-propanesulfonamide is obtained from 4-dimethylaminobutyryl-Pla-Gly-OH and N-(2S-isopropyl-4-oxo-5S-amino-6-cyclohexylhexyl)-propanesulfonamide.

b) A solution of 1 g of the abovementioned keto amide in 25 ml of $CH_3OH$ is hydrogenated on 0.1 g of 10% Pd-C at 20° and 1 bar until $H_2$ uptake ceases. Filtration and evaporation result in a mixture of N-[2S-isopropyl-4R- and -4S-hydroxy-5S-(4-dimethylaminobutyryl-Pla-Gly-amino)-6-cyclohexylhexyl]-propanesulfonamide.

EXAMPLE 13

70 mg of hydroxylamine hydrochloride are added to a solution of 627 mg of the keto amide obtainable as in Example 12a) and 1.43 g of $Na_2CO_3$. 10 $H_2O$ in 5 ml of methanol and 5 ml of water, and the mixture is stirred at 20° for 14 h. The precipitated oxime is filtered off, dried, dissolved in 10 ml of methanol and hydrogenated on 0.5 g of Raney Ni at 20° and 5 bar. The catalyst is filtered off, the filtrate is evaporated, the resulting mixture is separated on silica gel, and N-[2S-isopropyl-4S-amino-5S-(4-dimethylaminobutyryl-Pla-Gly-amino)-6-cyclohexylhexyl]-propanesulfonamide is obtained; the 4R-amino epimer is also obtained.

EXAMPLE 14

In analogy to Example 1, hydrogenolysis of N-ethyl-N'-[4S-hydroxy-5S-(morpholinocarbonyl-Pla-(imi-BOM-His)-amino)-6-cyclohexyl-hexyl]-urea yields N-ethyl-N'-[4S-hydroxy-5S-(morpholinocarbonyl-Pla-His-amino)-6-cyclohexyl-hexyl]-urea, hydrochloride, m.p. 126°–127°.

EXAMPLE 15

In analogy to Example 8, cleavage of N-ethyl-N'[4X-hydroxy-5S-(BOC-Pla-(S-Me-Cys)-amino)-6-cyclohexyl-hexyl]urea yields N-ethyl-N'-[4S-hydroxy-5S-(H-Pla-(S-Me Cys)-amino)-6-cyclohexyl-hexyl]-urea, m.p. 125°–126°.

The examples which follow relate to pharmaceutical compositions.

Example A: Tablets

A mixture of 1 kg of N-[2S-isopropyl-4S-hydroxy-5S-(4-aminopiperidinocarbonyl-Pla-His-amino)-6-cyclohexylhexyl]propanesulfonamide bis-trifluoroacetate, 4 kg of lactose, 1.2 kg of maize starch, 200 g of tack and 100 g of magnesium stearate is compressed in a customary manner to give tablets in such a way that each tablet contains 100 mg of active compound.

Example B: Coated tablets

Tablets are compressed in analogy to Example A and are then coated i na customary manner with a coating composed of sucrose, maize starch, talc, tragacanth and colorant.

Example C: Capsules 500 g of N-Ethyl-N'-[2-isopropyl-4S-hydroxy-5S-(4-aminopiperidinocarbonyl-Pla-His-amino)-6-cyclohexylhexyl]urea bistrifluoroacetate are dispensed in a customary manner into hard gelatine capsules so that each capsule contains 500 mg of active compound.

Example D: Injection ampoules

A solution of 100 g of N-Ethyl-N'-[4S-hydroxy-5S-(4-aminopiperidinocarbonyl-Pla-(S-Me-Cys)-amino)-6-cyclohexylhexyl]-urea trifluoroacetate in 4 l of double distilled water is adjusted to pH 6.5 with 2 N hydrochloric acid, filtered sterile and dispensed into injection ampoules. These are lyophilized under sterile conditions and sealed sterile. Each injection ampoule contains 50 mg of active compound.

Example E: Suppositories

A mixture of 50 g of N-ethyl-N'-[4S-hydroxy-5S-(4-aminopiperidinocarbonyl-Pla-(S-Me-Cys)-amino)-6-cyclohexylhexyl]urea trifluoroacetate with 10 g of soya lecithin and 140 g of cocoa butter is melted, poured into moulds and left to cool. Each suppository contains 250 mg of active compound.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A glycolic acid compound of the formula I $$X-O-CR^1R^2-CO-Y-NR^3-CHR^4-CR^5-CH_2-CR^6R^7-Z$$

wherein

X is H, 4-BOC-amino-piperidinocarbonyl, 4-aminopiperidinocarbonyl or morpholino-carbonyl;

Y is 0 or 1 amino acid reside selected from the group comprising His, Leu and S-A-Cys;

Z is $-CH_2-NH-SO_2R^{14}$, $-CH_2-NH-COR^{14}$, $-CH_2-NH-CO-NH-R^{14}$ or $-CH_2-NH-CS-NH-R^{14}$;

$R^1$, $R^3$ and $R^7$ and each H;

$R^2$ is benzyl;

$R^4$ is cyclohexylmethyl;

$R^5$ is (H, OH);

$R^6$ and $R^{14}$ are each independently H or A; and

A is alkyl having 1–4 C atoms.

2. A compound according to claim 1, wherein said compound is a) N-[2-Isopropyl-4-hydroxy-5-(4-aminopiperidinocarbonyl-Pla-His-amino)-6-cyclohexylhexyl]propanesulfonamide;

b) N-Ethyl-N'-[4-hydroxy-5-(4-aminopiperidinocarbonyl-Pla-His-amino)-6-cyclohexylhexyl]urea; or
c) N-Ethyl-N'-[4-hydroxy-5-(4-aminopiperidinocarbonyl-Pla-(S-Me-Cys)-amino)-6-cyclohexylhexyl]urea.

3. A compound according to claim 1, wherein X is 4-BOC-amino-piperidinocarbonyl, 4-aminopiperidinocarbonyl, or morpholino-carbonyl.

4. A compound according to claim 1, wherein Y is His, Leu or S-Me-Cys.

5. A compound according to claim 1, wherein X is 4-BOC-amino-piperidinocarbonyl.

6. A compound according to claim 1, wherein X is 4-amino-piperidinocarbonyl.

7. A compound according to claim 1, wherein X is morpholinyl-carbonyl.

8. A compound according to claim 1, wherein Y is His.

9. A compound according to claim 1, wherein Y is Leu.

10. A compound according to claim 1, wherein Y is S-A-Cys.

11. A compound according to claim 1, wherein Z is —CH$_2$—NH—CO—NH—R$^{14}$.

12. A compound according to claim 1, wherein said compound is:
N-[2R-methyl-4S-hydroxy-5S-(4-BOC-aminopiperidinocarbonyl-Pla-His-amino)-6-cyclohexylhexyl]propanesulfonamide,
N-Ethyl-N'-[4S-hydroxy-5S-(4-BOC-aminopiperidinocarbonyl-Pla-His-amino)-6-cyclohexylhexyl]urea,
N-[4S-Hydroxy-5S-(4-BOC-aminopiperidinocarbonyl-Pla-His-amino)-6-cyclohexylhexyl]propanesulfonamide,
N-Isopropyl-N'-[2R-methyl-4S-hydroxy-5S-(4-BOC-aminopiperidinocarbonyl-Pla-His-amino)-6-cyclohexylhexyl]urea,
N-Isopropyl-N'-[4S-hydroxy-5S-(4-BOC-aminopiperidinocarbonyl-Pla-His-amino)-6-cyclohexylhexyl]urea,
N-[4S-Hydroxy-5S-(4BOC-aminopiperidinocarbonyl-Pla-His-amino)-6-cyclohexylhexyl]urea,
N-ethyl-N'-[4S-hydroxy-5S-(4-aminopiperidinocarbonyl-Pla-His-amino)-6-cyclohexylhexyl]urea,
N-[2R-Methyl-4S-hydroxy-5S-(4-aminopiperidinocarbonyl-Pla-His-amino)-6-cyclohexylhexyl]propanesulfonamide,
N-Isopropyl-N'-[2R-methyl-4S-hydroxy-5S-(4-aminopiperidinocarbonyl-Pla-His-amino)-6-cyclohexylhexyl]urea,
N-[2S-isopropyl-4S-hydroxy-5S-(4-aminopiperidinocarbonyl-Pla-His-amino)-6-cyclohexylhexyl]propanesulfonamide,
N-Ethyl-N'-[4S-hydroxy-5S-(4-aminopiperidinocarbonyl-Pla-Leu-amino)-6-cyclohexylhexyl]urea,
N-[4S-Hydroxy-5S-(4-aminopiperidinocarbonyl-Pla-His-amino)-6-cyclohexylhexyl]isovaleramide,
N-Ethyl-N'-[2S-isopropyl-4S-hydroxy-5S-(4-aminopiperidinocarbonyl-Pla-His-amino)-6-cyclohexylhexyl]urea,
N-Ethyl-N'-[2S-isopropyl-4S-hydroxy-5S-(4-aminopiperidinocarbonyl-Pla-(S-Me-Cys)-amino)-6-cyclohexylhexyl]-urea,
N-Ethyl-N'-[4S-hydroxy-5S-(4-aminopiperidinocarbonyl-Pla-(S-Me-Cys)-amino)-6-cyclohexylhexyl]urea,
N-Ethyl-N'-[4S-hydroxy-5S-(4-BOC-aminopiperidinocarbonyl-Pla-(S-Me-Cys)-amino)-6-cyclohexylhexyl]thiourea,
N-Ethyl-N'-[4S-hydroxy-5S-(morpholinocarbonyl-Pla-(S-Me-Cys)amino)-6-cyclohexylhexyl]urea, or
N-ethyl-N'-[4S-hydroxy-5S-(H-Pla-(S-Me Cys)-amino)-6-cyclohexylhexyl]urea.

13. A method of diagnosing renin as a contributing factor in hypertension comprising administering to a subject suffering from hypertension 0.1–10 mg/kg of body weight of a compound according to claim 1.

14. A compound according to claim 1, wherein
X is 4-BOC-aminopiperidinocarbonyl or 4-aminopiperidinocarbonyl,
R$^1$, R$^3$ and R$^7$ are each H,
R$^2$ is benzyl,
R$^4$ is cyclohexylmethyl,
R$^5$ is (H, OH),
R$^6$ is H or A,
Z is —CH$_2$NHSO$_2$—A, —CH$_2$NHCONHR$^{14}$ or —CH$_2$NHCOA, and
R$^{14}$ is H or A.

15. A pharmaceutical composition comprising a compound according to claim 1 and a pharmaceutically acceptable carrier.

16. A composition according to claim 15, wherein said compound is in an amount of about 10 mg-1 g.

17. A method of treating renin-dependent hypertension or renin-dependent hyperaldosteronism comprising administering to a subject an effective amount of a compound of claim 1.

18. A method according to claim 17, comprising administering said compound in an amount of about 1–300 mg/kg of body weight.

19. A method of treating or prophylaxis of renin-dependent hypertension, renin-dependent cardiac insufficiency or renin-dependent hyperaldosteronism, comprising administering to a subject an effective amount of a compound of claim 1.

20. A method according to claim 19, comprising administering said compound in an amount of about 0.2–20 mg/kg of body weight.

* * * * *